(12) United States Patent
Horecka et al.

(10) Patent No.: US 7,608,415 B2
(45) Date of Patent: Oct. 27, 2009

(54) ANALYSIS OF INTRACELLULAR MODIFICATIONS

(75) Inventors: Joseph Horecka, Fremont, CA (US); Peter Fung, Sunnyvale, CA (US); Richard M. Eglen, Los Altos, CA (US)

(73) Assignee: Discoverx Corporation, Fremont, CA (US)

( * ) Notice: Subject to any disclaimer, the term of this patent is extended or adjusted under 35 U.S.C. 154(b) by 0 days.

(21) Appl. No.: 11/170,123

(22) Filed: Jun. 29, 2005

(65) Prior Publication Data

US 2006/0019285 A1 Jan. 26, 2006

Related U.S. Application Data

(60) Provisional application No. 60/584,709, filed on Jun. 30, 2004.

(51) Int. Cl.
C12Q 1/34 (2006.01)
C12Q 1/00 (2006.01)
C12N 9/24 (2006.01)

(52) U.S. Cl. .............................. 435/18; 435/4; 435/200

(58) Field of Classification Search ...................... 435/6, 435/7.1, 7.2, 7.21, 7.92, 200, 207, 69.1, 320.1; 536/23.1, 23.2, 23.4
See application file for complete search history.

(56) References Cited

U.S. PATENT DOCUMENTS

| | | | |
|---|---|---|---|
| 3,817,837 A | 6/1974 | Rubenstein et al. |
| 3,852,157 A | 12/1974 | Rubenstein et al. |
| 3,875,011 A | 4/1975 | Rubenstein et al. |
| 3,905,871 A | 9/1975 | Rubenstein et al. |
| 3,935,074 A | 1/1976 | Rubenstein et al. |
| 3,966,556 A | 6/1976 | Rubenstein et al. |
| 3,996,345 A | 12/1976 | Ullman |
| 3,998,943 A | 12/1976 | Ullman |
| 4,039,385 A | 8/1977 | Ullman et al. |
| 4,040,907 A | 8/1977 | Ullman et al. |
| 4,043,872 A | 8/1977 | Blakemore et al. |
| 4,046,636 A | 9/1977 | Ullman et al. |
| 4,065,354 A | 12/1977 | Ullman et al. |
| 4,067,774 A | 1/1978 | Rubenstein et al. |
| 4,130,462 A | 12/1978 | Rubenstein et al. |
| 4,134,792 A | 1/1979 | Bogulaski et al. |
| 4,160,016 A | 7/1979 | Ullman et al. |
| 4,160,645 A | 7/1979 | Ullman |
| 4,161,515 A | 7/1979 | Ullman et al. |
| 4,171,244 A | 10/1979 | Blakemore et al. |
| 4,174,384 A | 11/1979 | Ullman et al. |
| 4,191,613 A | 3/1980 | Ullman et al. |
| 4,193,983 A | 3/1980 | Ullman et al. |
| 4,208,479 A | 6/1980 | Zuk et al. |
| 4,213,893 A | 7/1980 | Carrico et al. |
| 4,318,980 A | 3/1982 | Bogulaski et al. |
| 4,318,983 A | 3/1982 | Hornby et al. |
| 4,378,428 A | 3/1983 | Farina et al. |
| 4,708,929 A | 11/1987 | Henderson |
| 4,956,274 A | 9/1990 | Khanna et al. |
| 6,770,451 B2 | 8/2004 | Rouhani et al. |
| 7,135,325 B2 | 11/2006 | Naqvi et al. |
| 2003/0092070 A1 | 5/2003 | Zhao et al. |
| 2004/0018562 A1 | 1/2004 | Rouhani et al. |
| 2004/0137480 A1 | 7/2004 | Eglen |
| 2005/0136488 A1 | 6/2005 | Horecka et al. |
| 2006/0105377 A1 | 5/2006 | Eglen |
| 2006/0199238 A1 | 9/2006 | Charter et al. |
| 2006/0292656 A1 | 12/2006 | Singh et al. |
| 2007/0015232 A1 | 1/2007 | Olson et al. |

FOREIGN PATENT DOCUMENTS

| | | | |
|---|---|---|---|
| EP | 0 551 842 A2 | | 7/1993 |
| WO | WO/03/021265 | * | 3/2003 |
| WO | WO 03/021265 A1 | | 3/2003 |
| WO | WO 2004/009794 A2 | | 1/2004 |

OTHER PUBLICATIONS

William A. Mohler, et al., Gene Expression and Cell Fusion Analzyed by *lacZ* Complementation in Mammalian Cells, *Proc. Natl. Acad. Sci.* Oct. 1996, 93:12423-12427, Genetics.
Peter Moosmann, et al., Alpha Complementation of LacZ in Mammalian Cells, *Nucleic Acids Research*, 1996, 24/6:1171-1172.
Fabio Rossi, et al., Monitoring Protein-Protein Interactions in Intact Eukaryotic Cells by β-galactosidase Complementation, *Proc. Natl. Acad. Sci.*, Aug. 1997, 94:8405-8410, Biochemistry.
Daniel R. Henderson, et al., Cedia™, A New Homogeneous Immunoassay System, 1986, *Clin. Chem.*, 32/9:1637-1641.
Richard M. Eglen, "Enzyme Fragment Complementation: A Flexible High Throughput Screening Assay Technology," Assay and Drug Development Technologies, 2002, vol. 1, No. 1-1, 97-104.
Richard M. Eglen, et al., "B Galactosidase Enzyme Fragment Complementation as A Novel Technology for High Throughput Screening," Combinatorial Chemistry & High Throughput Screening, 2003, vol. 6, 381-387.
EP Supplemental Search Report, Jan. 19, 2009, received Feb. 4, 2009.

* cited by examiner

Primary Examiner—Nashaat T Nashed
Assistant Examiner—Iqbal H Chowdhury

(57) ABSTRACT

Improved methods of determining the intracellular state of a protein as well as modifications of the protein are provided by introducing a surrogate fusion protein comprising a member of an enzyme fragment complementation complex and a target protein. After exposing cells transformed with the surrogate fusion protein to a change in environment, e.g. a candidate drug, the cells are lysed, the lysate separated into fractions or bands, conveniently by gel electrophoresis and transferring the proteins by Western blot to a membrane. The bands on the membrane are developed using the other member of the enzyme fragment complementation complex and a substrate providing a detectable signal. The method is found to provide high sensitivity and the ability to observe modifications of the target protein.

10 Claims, 7 Drawing Sheets

SEQUENCE LISTING

```
<160> NUMBER OF SEQ ID NOS: 5

<210> SEQ ID NO 1
<211> LENGTH: 4181
<212> TYPE: DNA
<213> ORGANISM: Artificial Sequence
<220> FEATURE:
<223> OTHER INFORMATION: Description of Artificial Sequence: Synthetic
      cloning vector

<400> SEQUENCE: 1
tagttattaa   tagtaatcaa   ttacggggtc   attagttcat   agcccatata   tggagttccg       60
cgttacataa   cttacggtaa   atggcccgcc   tggctgaccg   cccaacgacc   cccgcccatt      120
gacgtcaata   atgacgtatg   ttcccatagt   aacgccaata   gggactttcc   attgacgtca      180
atgggtggag   tatttacggt   aaactgccca   cttggcagta   catcaagtgt   atcatatgcc      240
aagtacgccc   cctattgacg   tcaatgacgg   taaatggccc   gcctggcatt   atgcccagta      300
catgacctta   tgggactttc   ctacttggca   gtacatctac   gtattagtca   tcgctattac      360
catggtgatg   cggttttggc   agtacatcaa   tgggcgtgga   tagcggtttg   actcacgggg      420
```

```
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cgtcagatcc gctagcgcta      600
ccggtcgcca ccatgagctc caattcactg gccgtcgttt tacaacgtcg tgactgggaa      660
aaccctggcg ttacccaact taatcgcctt gcagcacatc ccctttcgc cagctggcgt       720 aatagcgaag aggcccgcac cgatcgccct tcccaacagt tgcgcagcct gaatggcgaa      780
ccggactcag atctcgagct caagcttcga attctgcagt cgacggtacc gcgggcccgg      840
gatccaccgg atctagataa ctgatcataa tcagccatac cacatttgta gaggttttac      900
ttgctttaaa aaacctccca cacctccccc tgaacctgaa acataaaatg aatgcaattg      960
ttgttgttaa cttgtttatt gcagcttata atggttacaa ataaagcaat agcatcacaa     1020
atttcacaaa taaagcattt ttttcactgc attctagttg tggtttgtcc aaactcatca     1080
atgtatctta acgcgtaaat tgtaagcgtt aatattttgt taaaattcgc gttaaatttt     1140
tgttaaatca gctcattttt taaccaatag gccgaaatcg gcaaaatccc ttataaatca     1200
aaagaataga ccgagatagg gttgagtgtt gttccagttt ggaacaagag tccactatta     1260
aagaacgtgg actccaacgt caaagggcga aaaaccgtct atcagggcga tggcccacta     1320
cgtgaaccat cacccctaatc aagttttttg gggtcgaggt gccgtaaagc actaaatcgg     1380
aaccctaaag ggagccccccg atttagagct tgacggggaa agccggcgaa cgtggcgaga     1440
aaggaaggga agaaagcgaa aggagcgggc gctagggcgc tggcaagtgt agcggtcacg     1500
ctgcgcgtaa ccaccacacc cgccgcgctt aatgcgccgc tacagggcgc gtcaggtggc     1560
acttttcggg gaaatgtgcg cggaacccct atttgtttat ttttctaaat acattcaaat     1620
atgtatccgc tcatgagaca ataaccctga taaatgcttc aataatattg aaaaaggaag     1680
agtcctgagg cggaaagaac cagctgtgga atgtgtgtca gttagggtgt ggaaagtccc     1740
caggctcccc agcaggcaga agtatgcaaa gcatgcatct caattagtca gcaaccaggt     1800
gtggaaagtc cccaggctcc ccagcaggca gaagtatgca aagcatgcat ctcaattagt     1860
cagcaaccat agtcccgccc ctaactccgc ccatcccgcc cctaactccg cccagttccg     1920
cccattctcc gccccatggc tgactaattt ttttttattta gcagaggcc gaggccgcct     1980 cggcctctga gctattccag aagtagtgag gaggcttttt tggaggccta ggcttttgca     2040
aagatcgatc aagagacagg atgaggatcg tttcgcatga ttgaacaaga tggattgcac     2100
gcaggttctc cggccgcttg ggtggagagg ctattcggct atgactgggc acaacagaca     2160
atcggctgct ctgatgccgc cgtgttccgg ctgtcagcgc aggggcgccc ggttcttttt     2220
gtcaagaccg acctgtccgg tgccctgaat gaactgcaag acgaggcagc gcggctatcg     2280
tggctggcca cgacgggcgt tccttgcgca gctgtgctcg acgttgtcac tgaagcggga     2340
agggactggc tgctattggg cgaagtgccg gggcaggatc tcctgtcatc tcaccttgct     2400
cctgccgaga aagtatccat catggctgat gcaatgcggc ggctgcatac gcttgatccg     2460
gctacctgcc cattcgacca ccaagcgaaa catcgcatcg agcgagcacg tactcggatg     2520
gaagccggtc ttgtcgatca ggatgatctg gacgaagagc atcaggggct cgcgccagcc     2580
gaactgttcg ccaggctcaa ggcgagcatg cccgacggcg aggatctcgt cgtgacccat     2640
ggcgatgcct gcttgccgaa tatcatggtg aaaatggcc gcttttctgg attcatcgac     2700
tgtggccggc tgggtgtggc ggaccgctat caggacatag cgttggctac ccgtgatatt     2760
gctgaagagc ttggcggcga atgggctgac cgcttcctcg tgctttacgg tatcgccgct     2820
```

```
cccgattcgc agcgcatcgc cttctatcgc cttcttgacg agttcttctg agcgggactc    2880
tggggttcga atgaccgac caagcgacgc ccaacctgcc atcacgagat ttcgattcca     2940
ccgccgcctt ctatgaaagg ttgggcttcg gaatcgtttt ccgggacgcc ggctggatga    3000
tcctccagcg cggggatctc atgctggagt tcttcgccca ccctaggggg aggctaactg    3060
aaacacggaa ggagacaata ccggaaggaa cccgcgctat gacggcaata aaagacaga    3120 ataaaacgca cggtgttggg tcgtttgttc ataaacgcgg ggttcggtcc cagggctggc    3180
actctgtcga taccccaccg agaccccatt ggggccaata cgcccgcgtt tcttcctttt    3240
ccccacccca cccccaagt tcgggtgaag gcccagggct cgcagccaac gtcggggcgg     3300
caggccctgc catagcctca ggttactcat atatacttta gattgattta aaacttcatt    3360
tttaatttaa aaggatctag gtgaagatcc tttttgataa tctcatgacc aaaatccctt    3420
aacgtgagtt ttcgttccac tgagcgtcag accccgtaga aaagatcaaa ggatcttctt    3480
gagatccttt ttttctgcgc gtaatctgct gcttgcaaac aaaaaaacca ccgctaccag    3540
cggtggtttg tttgccggat caagagctac caactctttt tccgaaggta actggcttca    3600
gcagagcgca gataccaaat actgtccttc tagtgtagcc gtagttaggc caccacttca    3660
agaactctgt agcaccgcct acatacctcg ctctgctaat cctgttacca gtggctgctg    3720
ccagtggcga taagtcgtgt cttaccgggt tggactcaag acgatagtta ccggataagg    3780
cgcagcggtc gggctgaacg gggggttcgt gcacacagcc cagcttggag cgaacgacct    3840
acaccgaact gagataccta cagcgtgagc tatgagaaag cgccacgctt cccgaaggga    3900
gaaaggcgga caggtatccg gtaagcggca gggtcggaac aggagagcgc acagggagc    3960 ttccaggggg aaacgcctgg tatctttata gtcctgtcgg gtttcgccac ctctgacttg    4020
agcgtcgatt tttgtgatgc tcgtcagggg ggcggagcct atggaaaaac gccagcaacg    4080 cggcctttt acgttcctg gccttttgct ggccttttgc tcacatgttc tttcctgcgt     4140
tatcccctga ttctgtggat aaccgtatta ccgccatgca t                       4181
```

<210> SEQ ID NO 2
<211> LENGTH: 4183
<212> TYPE: DNA
<213> ORGANISM: Artificial Sequence
<220> FEATURE:
<223> OTHER INFORMATION: Description of Artificial Sequence: Synthetic cloning vector

<400> SEQUENCE: 2

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
```

```
gatccaccgg tcgccaccat gagctccaat tcactggccg tcgttttaca acgtcgtgac    720
tgggaaaacc ctggcgttac ccaacttaat cgccttgcag cacatccccc tttcgccagc    780
tggcgtaata gcgaagaggc ccgcaccgat cgcccttccc aacagttgcg cagcctgaat    840
ggcgaatagg cggccgcgac tctagatcat aatcagccat accacatttg tagaggtttt    900
acttgcttta aaaaacctcc cacacctccc cctgaacctg aaacataaaa tgaatgcaat    960
tgttgttgtt aacttgttta ttgcagctta taatggttac aaataaagca atagcatcac   1020
aaatttcaca aataaagcat ttttttcact gcattctagt tgtggtttgt ccaaactcat   1080
caatgtatct taaggcgtaa attgtaagcg ttaatatttt gttaaaattc gcgttaaatt   1140
tttgttaaat cagctcattt tttaaccaat aggccgaaat cggcaaaatc ccttataaat   1200
caaaagaata gaccgagata gggttgagtg ttgttccagt ttggaacaag agtccactat   1260
taaagaacgt ggactccaac gtcaaagggc gaaaaaccgt ctatcagggc gatggcccac   1320
tacgtgaacc atcaccctaa tcaagttttt tggggtcgag gtgccgtaaa gcactaaatc   1380
ggaaccctaa agggagcccc cgatttagag cttgacgggg aaagccggcg aacgtggcga   1440
gaaaggaagg gaagaaagcg aaaggagcgg gcgctagggc gctggcaagt gtagcggtca   1500
cgctgcgcgt aaccaccaca cccgccgcgc ttaatgcgcc gctacagggc gcgtcaggtg   1560
gcacttttcg gggaaatgtg cgcggaaccc ctatttgttt attttctaa atacattcaa    1620
atatgtatcc gctcatgaga caataaccct gataaatgct tcaataatat tgaaaaagga   1680
agagtcctga ggcggaaaga accagctgtg gaatgtgtgt cagttagggt gtggaaagtc   1740
cccaggctcc ccagcaggca gaagtatgca aagcatgcat ctcaattagt cagcaaccag   1800
gtgtggaaag tccccaggct ccccagcagg cagaagtatg caaagcatgc atctcaatta   1860
gtcagcaacc atagtcccgc ccctaactcc gcccatcccg ccctaactc gcccagttc    1920
cgcccattct ccgccccatg gctgactaat ttttttatt tatgcagagg ccgaggccgc   1980
ctcggcctct gagctattcc agaagtagtg aggaggcttt tttggaggcc taggcttttg   2040
caaagatcga tcaagagaca ggatgaggat cgtttcgcat gattgaacaa gatggattgc   2100
acgcaggttc tccggccgct tgggtggaga ggctattcgg ctatgactgg gcacaacaga   2160
caatcggctg ctctgatgcc gccgtgttcc ggctgtcagc gcaggggcgc ccggttcttt   2220
ttgtcaagac cgacctgtcc ggtgccctga atgaactgca agacgaggca gcgcggctat   2280
cgtggctggc cacgacgggc gttccttgcg cagctgtgct cgacgttgtc actgaagcgg   2340
gaagggactg gctgctattg ggcgaagtgc cggggcagga tctcctgtca tctcaccttg   2400
ctcctgccga gaaagtatcc atcatggctg atgcaatgcg gcggctgcat acgcttgatc   2460
cggctacctg cccattcgac caccaagcga aacatcgcat cgagcgagca cgtactcgga   2520
tggaagccgg tcttgtcgat caggatgatc tggacgaaga gcatcagggg ctcgcgccag   2580
ccgaactgtt cgccaggctc aaggcgagca tgcccgacgg cgaggatctc gtcgtgaccc   2640
atggcgatgc ctgcttgccg aatatcatgg tggaaaatgg ccgcttttct ggattcatcg   2700
actgtggccg gctgggtgtg gcggaccgct atcaggacat agcgttggct acccgtgata   2760
ttgctgaaga gcttggcggc gaatgggctg accgcttcct cgtgctttac ggtatcgccg   2820
ctcccgattc gcagcgcatc gccttctatc gccttcttga cgagttcttc tgagcgggac   2880
tctgggttc gaaatgaccg accaagcgac gcccaacctg ccatcacgag atttcgattc   2940
caccgccgcc ttctatgaaa ggttgggctt cggaatcgtt ttccgggacg ccggctggat   3000
```

-continued

```
gatcctccag cgcggggatc tcatgctgga gttcttcgcc cacccctaggg ggaggctaac    3060 tgaaacacgg aaggagacaa taccggaagg aacccgcgct atgacggcaa taaaaagaca    3120
gaataaaacg cacggtgttg ggtcgtttgt tcataaacgc ggggttcggt cccagggctg    3180
gcactctgtc gatacccccac cgagacccca ttggggccaa tacgcccgcg tttcttcctt    3240
ttccccaccc caccccccaa gttcgggtga aggcccaggg ctcgcagcca acgtcgggc    3300 ggcaggccct gccatagcct caggttactc atatatactt tagattgatt taaaacttca    3360 ttttttaattt aaaaggatct aggtgaagat ccttttgat aatctcatga ccaaaatccc    3420
ttaacgtgag ttttcgttcc actgagcgtc agaccccgta gaaaagatca aaggatcttc    3480
ttgagatcct ttttttctgc gcgtaatctg ctgcttgcaa acaaaaaaac caccgctacc    3540
agcggtggtt tgtttgccgg atcaagagct accaactctt tttccgaagg taactggctt    3600
cagcagagcg cagataccaa atactgtcct tctagtgtag ccgtagttag gccaccactt    3660
caagaactct gtagcaccgc ctacatacct cgctctgcta atcctgttac cagtggctgc    3720
tgccagtggc gataagtcgt gtcttaccgg gttggactca agacgatagt taccggataa    3780
ggcgcagcgg tcgggctgaa cggggggttc gtgcacacag cccagcttgg agcgaacgac    3840
ctacaccgaa ctgagatacc tacagcgtga gctatgagaa agcgccacgc ttcccgaagg    3900
gagaaaggcg gacaggtatc cggtaagcgg caggtcgga acaggagagc gcacgaggga    3960
gcttccaggg ggaaacgcct ggtatcttta tagtcctgtc gggtttcgcc acctctgact    4020
tgagcgtcga ttttgtgat gctcgtcagg ggggcggagc ctatggaaaa acgccagcaa    4080
cgcggccttt ttacggttcc tggccttttg ctggccttttt gctcacatgt tctttcctgc    4140
gttatcccct gattctgtgg ataaccgtat taccgccatg cat                      4183
```

<210> SEQ ID NO 3
<211> LENGTH: 479
<212> TYPE: PRT
<213> ORGANISM: Homo sapiens

<400> SEQUENCE: 3

```
Met Ser Ser Asn Ser Leu Ala Val Val Leu Gln Arg Arg Asp Trp Glu
 1               5                  10                  15

Asn Pro Gly Val Thr Gln Leu Asn Arg Leu Ala Ala His Pro Pro Phe
            20                  25                  30

Ala Ser Trp Arg Asn Ser Glu Glu Ala Arg Thr Asp Arg Pro Ser Gln
        35                  40                  45

Gln Leu Arg Ser Leu Asn Gly Glu Pro Asp Ser Asp Leu Glu Gln Lys
    50                  55                  60

Leu Ile Ser Glu Glu Asp Leu Gly Glu Lys Pro Gly Thr Arg Val Phe
65                  70                  75                  80

Lys Lys Ser Ser Pro Asn Cys Lys Leu Thr Val Tyr Leu Gly Lys Arg
                85                  90                  95

Asp Phe Val Asp His Leu Asp Lys Val Asp Pro Val Asp Gly Val Val
            100                 105                 110

Leu Val Asp Pro Asp Tyr Leu Lys Asp Arg Lys Val Phe Val Thr Leu
        115                 120                 125

Thr Cys Ala Phe Arg Tyr Gly Arg Glu Asp Leu Asp Val Leu Gly Leu
    130                 135                 140

Ser Phe Arg Lys Asp Leu Phe Ile Ala Thr Tyr Gln Ala Phe Pro Pro
145                 150                 155                 160

Val Pro Asn Pro Pro Arg Pro Pro Thr Arg Leu Gln Asp Arg Leu Leu
```

```
                      165                 170                 175
Arg Lys Leu Gly Gln His Ala His Pro Phe Phe Thr Ile Pro Gln
            180                 185                 190

Asn Leu Pro Cys Ser Val Thr Leu Gln Pro Gly Pro Glu Asp Thr Gly
            195                 200                 205

Lys Ala Cys Gly Val Asp Phe Glu Ile Arg Ala Phe Cys Ala Lys Ser
            210                 215                 220

Leu Glu Glu Lys Ser His Lys Arg Asn Ser Val Arg Leu Val Ile Arg
225                 230                 235                 240

Lys Val Gln Phe Ala Pro Glu Lys Pro Gly Pro Gln Pro Ser Ala Glu
                245                 250                 255

Thr Thr Arg His Phe Leu Met Ser Asp Arg Ser Leu His Leu Glu Ala
                260                 265                 270

Ser Leu Asp Lys Glu Leu Tyr Tyr His Gly Glu Pro Leu Asn Val Asn
            275                 280                 285

Val His Val Thr Asn Asn Ser Thr Lys Thr Val Lys Lys Ile Lys Val
            290                 295                 300

Ser Val Arg Gln Tyr Ala Asp Ile Cys Leu Phe Ser Thr Ala Gln Tyr
305                 310                 315                 320

Lys Cys Pro Val Ala Gln Leu Glu Gln Asp Asp Gln Val Ser Pro Ser
                325                 330                 335

Ser Thr Phe Cys Lys Val Tyr Thr Ile Thr Pro Leu Leu Ser Asp Asn
                340                 345                 350

Arg Glu Lys Arg Gly Leu Ala Leu Asp Gly Lys Leu Lys His Glu Asp
            355                 360                 365

Thr Asn Leu Ala Ser Ser Thr Ile Val Lys Glu Gly Ala Asn Lys Glu
            370                 375                 380

Val Leu Gly Ile Leu Val Ser Tyr Arg Val Lys Val Lys Leu Val Val
385                 390                 395                 400

Ser Arg Gly Gly Asp Val Ser Val Glu Leu Pro Phe Val Leu Met His
                405                 410                 415

Pro Lys Pro His Asp His Ile Pro Leu Pro Arg Pro Gln Ser Ala Ala
                420                 425                 430

Pro Glu Thr Asp Val Pro Val Asp Thr Asn Leu Ile Glu Phe Asp Thr
            435                 440                 445

Asn Tyr Ala Thr Asp Asp Asp Ile Val Phe Glu Asp Phe Ala Arg Leu
            450                 455                 460

Arg Leu Lys Gly Met Lys Asp Asp Tyr Asp Asp Gln Leu Cys
465                 470                 475

<210> SEQ ID NO 4
<211> LENGTH: 492
<212> TYPE: PRT
<213> ORGANISM: Homo sapiens

<400> SEQUENCE: 4

Met Gly Glu Lys Pro Gly Thr Arg Val Phe Lys Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
            35                  40                  45

Leu Lys Asp Arg Lys Val Phe Val Thr Leu Thr Cys Ala Phe Arg Tyr
        50                  55                  60
```

-continued

```
Gly Arg Glu Asp Leu Asp Val Leu Gly Leu Ser Phe Arg Lys Asp Leu
 65                  70                  75                  80

Phe Ile Ala Thr Tyr Gln Ala Phe Pro Pro Val Pro Asn Pro Pro Arg
                 85                  90                  95

Pro Pro Thr Arg Leu Gln Asp Arg Leu Leu Arg Lys Leu Gly Gln His
            100                 105                 110

Ala His Pro Phe Phe Phe Thr Ile Pro Gln Asn Leu Pro Cys Ser Val
        115                 120                 125

Thr Leu Gln Pro Gly Pro Glu Asp Thr Gly Lys Ala Cys Gly Val Asp
    130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
            180                 185                 190

Met Ser Asp Arg Ser Leu His Leu Glu Ala Ser Leu Asp Lys Glu Leu
        195                 200                 205

Tyr Tyr His Gly Glu Pro Leu Asn Val Asn Val His Val Thr Asn Asn
    210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
            260                 265                 270

Tyr Thr Ile Thr Pro Leu Leu Ser Asp Asn Arg Glu Lys Arg Gly Leu
        275                 280                 285

Ala Leu Asp Gly Lys Leu Lys His Glu Asp Thr Asn Leu Ala Ser Ser
    290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
            340                 345                 350

Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys Glu Gln Lys Leu Ile Ser Glu
                405                 410                 415

Glu Asp Leu Gly Ile Leu Gln Ser Thr Val Pro Arg Ala Arg Asp Pro
            420                 425                 430

Pro Val Ala Thr Met Ser Ser Asn Ser Leu Ala Val Val Leu Gln Arg
        435                 440                 445

Arg Asp Trp Glu Asn Pro Gly Val Thr Gln Leu Asn Arg Leu Ala Ala
    450                 455                 460

His Pro Pro Phe Ala Ser Trp Arg Asn Ser Glu Glu Ala Arg Thr Asp
465                 470                 475                 480

Arg Pro Ser Gln Gln Leu Arg Ser Leu Asn Gly Glu
```

```
<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      c-myc epitope tag

<400> SEQUENCE: 5

Glu Gln Lys Leu Ile Ser Glu Glu Asp Leu
 1               5                  10
```

ANALYSIS OF INTRACELLULAR MODIFICATIONS

CROSS-REFERENCE TO RELATED APPLICATIONS

This application claims priority from U.S. Provisional Patent Application No. 60/584,709 filed on Jun. 30, 2004, which is hereby incorporated by reference in its entirety.

REFERENCE TO SEQUENCE LISTING

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Technical Field

The field of this invention is proteomic assays.

2. Background

As more is learned about cellular pathways, the interactions of microorganisms with mammals, the growth and development of organisms, both prokaryotic and eukaryotic, there is an increasing need for improved methods of identifying protein members involved with these various processes. Also, as proteins and their function are identified, there is an increasing interest in being able to modulate the activity of proteins associated with diseased states. By screening for active compounds that modulate the activity, one is interested, not only in identifying the effect of the compound on the target protein, but also any effects the compound may have on other proteins present in the cell or medium.

There are numerous ways to separate components of a complex mixture based on differences in the components of mass, mass-to-charge, conformation, etc. Gel electrophoresis has been a major methodology for analyzing mixtures of proteins. Native proteins and denatured proteins are readily separated by their migration rate, which for the most part can be related to their molecular weight. Numerous techniques have been developed for identifying the separated protein bands. The Western blot was developed to identify proteins. As part of the Western blot, the proteins are separated by electrophoresis in a gel, followed by transfer of the protein bands to a membrane. The bands are then developed by various techniques, such as labeled antibodies or a non-specific protein dye. Other methods of separation include chromatography, e.g. HPLC, FPLC, capillary electrophoresis, etc.

The Western blot methodology has many desirable properties for identifying proteins in a mixture. However, even with 2D protocols, where one is dealing with a lysate or comparable mixture, there can be protein overlap, difficulties in detecting low amounts of a component, inadequate separations, inability to detect modifications of the protein and the like.

Today, one is interested in determining many aspects of the life of a protein in a cell, particularly in response to a change in the environment, e.g. a candidate compound as a drug. Proteins can undergo numerous modifications, such as partial or total degradation, glycosylation, ubiquitination, phosphorylation or dephosphorylation, acetylation, acylation, prenylation, etc. Being able to discern the existence of different aspects of the same protein is important in understanding pathways, such as identifying the major and minor status of the parent protein and the modified protein, where the effect of a candidate compound can be analyzed. Also, by being able to observe patterns of variations in the protein analogs and partial degradation products, one can identify cellular pathways and their interaction with other proteins.

There is, therefore, substantial interest in developing techniques that will allow the efficient investigation of cellular proteins, the effect of changes in the cellular environment on the protein, and being able to detect low levels of a protein of interest in the presence of large amounts of other proteins that may have analogous migration aptitudes.

Relevant Literature

U.S. Pat. Nos. 6,680,208 and 6,677,128 and WO94/29725 describe various Western blotting techniques. PCT/US02/27497 describes the use of fusion proteins employing enzyme fragmentation complexes for determining the status of the fusion protein in a cell.

SUMMARY OF THE INVENTION

The fate of cellular proteins is determined by employing a genetically modified cell expressing one or more proteins of interest fused to a fragment that is a member of an enzyme fragment complementation ("EFC") pair. The lysate of the cell is separated, conveniently employing Western blotting, and the fractions or bands developed using the other member of the EFC pair and a substrate. The observed fractions or bands are limited to those proteins that comprise the fused fragment, allowing for detection of any form of the protein(s) of interest that retains the fragment.

DESCRIPTION OF THE SPECIFIC EMBODIMENTS

Figure 1:
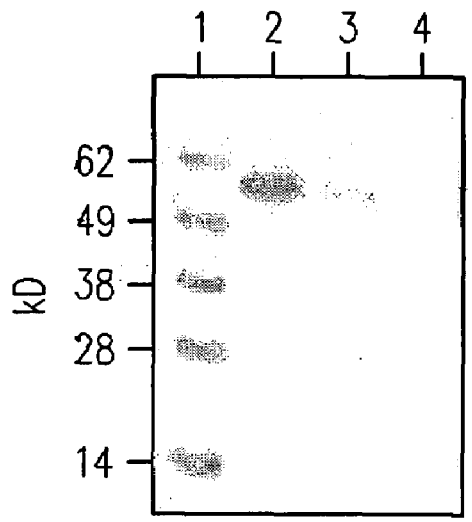
FIG. 1 shows the detection on blots of β-arrestin2 fusion proteins tagged with both ProLabel and the c-myc epitope. EAstern blots (upper panels) were photographed under white light after incubation with the chromogenic substrate X-Gal for the indicated times. 1A is an EAstern Blot with overnight incubation; 1B is an EAstern Blot with 2 day incubation; The Western blots (lower panels) were developed with the chemiluminescent substrate CDP-Star and detected with a CCD camera using the indicated exposure times. Lane 1, prestained MW marker (Invitrogen, Cat. No. LC5925). Lanes 2-4, lysates of CHO-K1 cells transiently transfected with plasmids pPL-myc-barr2, pbarr2-myc-PL, and pEGFP-C1, respectively; 1C is a Western Blot, PAb, 6 min incubation; 1D is a Western Blot, 12 minutes incubation.
Figure 1:
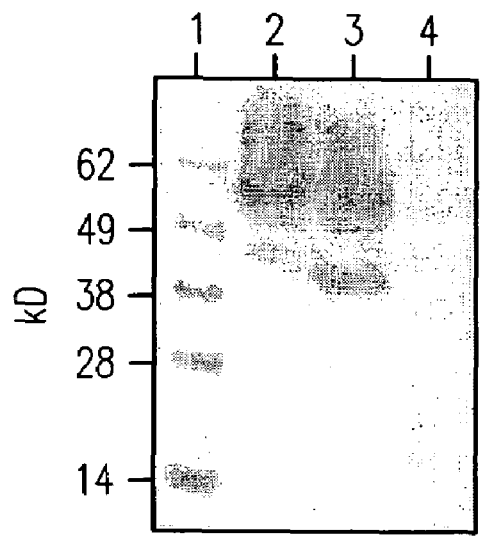
Figure 1:
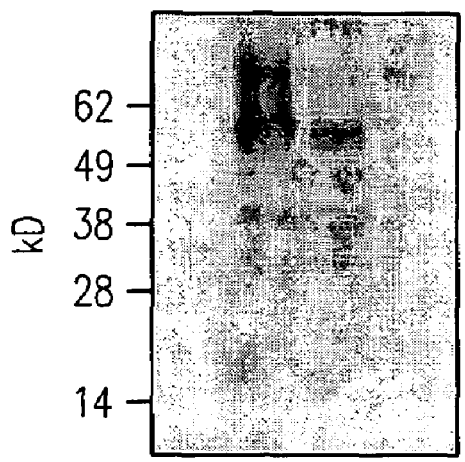
Figure 1:
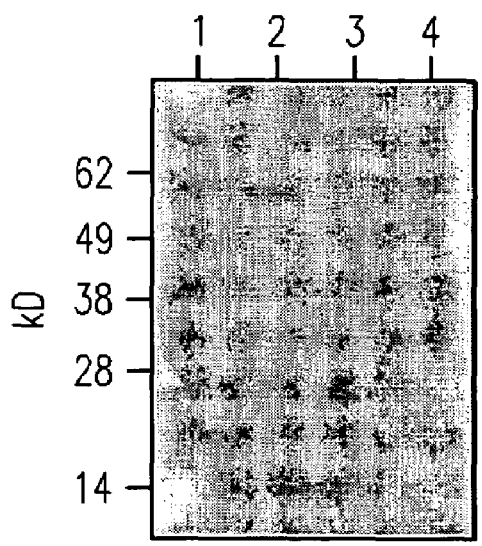

Methods and compositions are provided for determining the status of intracellular proteins by employing an enzyme fragment complementation ("EFC") pair. A genetically modified cell comprising a fusion protein comprising one member of the EFC pair and the protein(s) of interest is employed. The cells are lysed and the protein components separated using any separation method that allows for individual fractions of the different protein components retaining the member of the EFC pair. The use of gel electrophoresis and Western blotting has been found to be applicable and advantageous as compared to other methods of separation and isolation. The bands comprising the fusion protein(s), modified fusion protein(s) and degradation products containing the fragment are identified, conveniently with Western blotting, developed on the membrane using the other member of the EFC pair and a substrate for the enzyme.

The subject method finds particular interest in analyzing cellular pathways and evaluating the effect of a change in environment on the cellular pathways involving protein(s) of interest. The subject method is particularly useful in evaluating the effect of a change in environment, such as evaluation of a candidate drug for a specific target or for the effect on proteins other than the specific target. It finds application in research, high throughput screening, clinical studies, ADME, and the like.

The subject systems employ surrogate fusion proteins for determining cellular events, where the surrogate protein serves as a measure of the protein of interest. The system employs various methods and compositions for determining a cellular event, such as the status or state of a protein(s) of interest. Genetic expression constructs are provided for introducing the genetic construct into a target cell for expression of the fusion protein. The method relies upon the use of EFC pairs, where the holoenzyme is formed by combining the fusion protein or fragment thereof with the complementary member of the EFC.

Because of the convenience of gel electrophoresis and Western blotting in allowing one to view the various fractions simultaneously and compare their intensity, Western blotting is the preferred detection system. The membrane of the Western blot permits the simultaneous addition of the necessary reagents to the fusion protein and its fragments, so as to have a comparable concentration of the added reagents. In addition, one may also use antibody detection to compare the native protein with the fusion protein and its fragments. Therefore, gel electrophoresis will be described as paradigmatic of other methods of separation and isolation.

As used in this invention, gel electrophoresis and Western blotting will be referred to as the EAstern system in emphasizing that the EFC pair consists of an enzyme donor ("ED") and an enzyme acceptor ("EA"). The complexing of the ED and EA provide the active or holoenzyme. Events that result in (1) the expression of the fusion protein or (2) modification of the fusion protein with a change in migration rate of the ED can be measured as an indication of changes of the fusion protein in the cell.

Any small ED may be used that will allow for detection with an EA and is stable under the conditions of the assay. For the most part, the ED of β-galactosidase will be used, but other EDs such as the S-peptide from RNase or the like, can also find use. The ED will generally be at least about 35 amino acids and not more than about 100 amino acids, generally in the range of about 36 to 90 amino acids, preferably below about 75 amino acids.

In some instances it may not be necessary to use the entire target protein, since a portion of the target protein will suffice. Usually at least about 25% of the contiguous amino acids of the protein will be used. In some instances where a protein is processed to smaller fragments that have physiological activity, one may only encode the smaller fragment. In other instances, one may truncate the protein to use only a functional portion of the protein, e.g. the intracellular portion of a receptor.

After performing whatever changes, if any, in environment are to be evaluated, the cell is lysed and the components are separated using 1D or 2D electrophoresis, followed by Western blotting. The bands of the Western blot are contacted with an EA and a detectable substrate, where the enzyme activity is measured from the signal resulting from the enzymatic reaction of the substrate. The amount of enzyme product produced is related to the activity of the ED in binding to the EA. The different positions of the bands on the membrane indicate the changes in the fusion protein in the cells. Where one has changed the environment by, for example, the addition of a candidate drug, the changes can be related to the presence of the drug. The enzyme activity will be influenced by degradation of the fusion protein, binding of the fusion protein to a compound complexing with the protein of interest, modification of the fusion protein, and the like. The status of the fusion protein may be related to the level of activity of various cellular pathways, where the protein surrogate being measured is associated with a pathway. In this way one can measure the activation or inhibition of a pathway, where such change in the status of the pathway changes the activity and/or nature of the fusion protein.

In the electrophoretic gel separation, one may maintain the native nature of the protein or denature the protein using sodium dodecylsulfonate ("SDS"). In the former case, the migration rate will not only depend on size and charge, but also to some degree on conformation and interaction with other proteins, e.g. complexes of the fusion protein with other proteins. By contrast, with separation in the presence of SDS, most proteins will have the same charge-to-mass ratio and be separated primarily by size. Either technique may be employed, depending upon the information one wishes to obtain from the analysis.

Since the migration of the protein will be dependent on size and charge, changes in either or both of these will change the migration of the protein. In this way one can monitor changes in size by degradation, complexation, conjugation, such as glycosylation, ubiquitination, prenylation, isoamide formation, etc., changes in charge as a result of phosphorylation or dephosphorylation, similarly sulfation, amidification, acylation, etc. or the opposite, where a group is removed. One can analyze the band if the nature of the band is unknown or where known, the various changes in the protein can be readily determined by comparison with known proteins.

The changes in the migration of the protein can be a result of any of a number of processes that result in a size change. Some of these changes may also result in a change in the activity of the ED in forming an active complex with EA. In the process of degradation using polyubiquitination, a series of protein products may be formed prior to degradation by the proteasome. The subject method allows for analysis of these ubiquinated products and an estimate as to the amount of each of these products. In this way, one obtains a picture of the process of degradation and its progress. Alternatively, migration and activity can be modified as a result of complex formation between the protein of interest as represented by the fusion protein and another protein, modification of the fusion protein, partial degradation of the fusion protein, etc.

Other methods of separation by size and/or charge, such as chromatography, can also be used. By taking individual fractions off of a chromatographic column and adding the necessary reagents, any of the ED present can be determined. Where the individual fractions do not have a known migration rate on the column, the ED containing component may be analyzed. Where the migration rate is known, one can directly relate the amount of the component in the fraction to the particular form of the fusion protein. Use of FPLC is well established as to the packing of the column and the elution of fractions.

After lysing the cells and, for a Western blotting, separating the proteins by gel electrophoresis, the protein bands are transferred to a membrane in accordance with conventional procedures. Various buffers are available for carrying out the transfer and different membranes may be used for receiving the bands. Conventional membranes include membranes of nitrocellulose, nylon and PVDF. The particular membrane selected may vary with the nature of the proteins of interest and their effect on the assay. The bands are then transferred from the gel to the membrane retaining their position in relation to each other. Once the transfer is complete, the membrane is placed in an appropriate assay buffer containing EA and the enzyme complex allowed to form.

Buffer is conventional for the complex formation and the assay, generally comprising conventional buffers, such as PIPES, MOPS, HEPES, etc., at a concentration in the range of about 50-250 mM, NaCl in the range of about 250-500 mM, a metal chelating agent, e.g. EGTA, at about 2 to 20 mM, a non-ionic detergent, such as Tween, 5-25 mM Mg salt and a stabilizer, such as sodium azide at a concentration in the range of about 10-20 mM. The pH will be in the range of about 6.5 to 7.5. A conventional buffer has the composition: 100 mM PIPES, 400 mM NaCl, 10 mM EGTA, 0.005% Tween, 150 mM NaOH, 10 mM Mg acetate, 14.6 mM $NaN_3$, pH 6.9. Following the incubation with EA, a substrate is added, there being many convenient fluorescent and chemiluminescent substrates commercially available. After sufficient time for the detectable product to form, the positions of the bands can be visualized and analyzed.

The sensitivity of the assay is at least about 0.1 ng or less in a protein band, 0.09 ng bands having been observed. In this way, very small amounts of a modified protein may be detected, as well as very small amounts of the fusion protein. Where the fusion protein undergoes a variety of modifications, such as polyubiquitination, polyphosphorylation or dephosphorylation, etc., one has the opportunity to observe the different forms of the fusion protein and determine the amount of each of the entities.

The fusion protein gene expression construct may be used initially to determine whether the gene to be inserted results in a fusion protein that is biologically active to serve as a surrogate for the natural protein. Once it has been shown that the fusion protein can serve as a surrogate, the construct may then be used in analyzing the protein under conditions of interest.

The first component of the subject invention is the fusion protein and its expression construct. The ED may be at either the C-terminus, the N-terminus or internal to the fusion protein. The particular site of the ED in the fusion protein will depend upon the ability to include the ED in the coding sequence without significant reduction in the natural activity of the protein of interest, the effect of the position on the modifications of the protein, the nature of the degradation and the ability of the ED to complex with the EA to form an active enzyme. Thus, depending upon how much is known about the protein of interest, its structure, site(s) of binding to other entities, the folding pattern, as to loops, β-sheets and α-helices, the manner in which the ED activity will be modulated, e.g. degradation, steric interference of binding with EA by another entity, modification resulting in changes in conformation or charge, etc., the ED will be situated to provide the optimized response. For degradation, it may or may not matter at what site the ED is situated, this is also likely to be true in many cases for steric interference, so long as the fusion protein retains its natural conformation and susceptibility to degradation. However, for localized modification, such as phosphorylation or dephosphorylation, proteolytic cleavage for maturation, etc., usually it will be desirable to have the ED in a position that does not influence the modification. By knowing the structure of the protein, one can select loops, α-helices, β-sheets, sites of binding or the like to determine the site for insertion of the ED.

The ED may be inserted into the coding region in a variety of ways. For a cDNA gene, one may select a suitable restriction site for insertion of the sequence, where by using overhangs at the restriction site, the orientation is provided in the correct direction. Alternatively, one may use constructs that have homologous sequences with the target gene and allow for homologous recombination, where the homologous sequences that are adjacent in the target gene are separated by the ED in the construct. By using a plasmid in yeast having the cDNA gene, with or without an appropriate transcriptional and translational regulatory region, one may readily insert the ED construct into the cDNA gene at an appropriate site. Alternatively, one may insert the ED coding region with the appropriate splice sites in an intron or in an exon of the gene encoding the protein of interest. In this way, one can select for a site of introduction at any position in the protein. In some instances, it will be useful to make a number of constructs, where the ED is introduced into an intron and test the resulting proteins for ED activity and retention of function of the protein. Various other conventional ways for inserting encoding sequences into a gene can be employed. For expression constructs and decriptions of other conventional manipulative processes, see, e.g., Sambrook, Fritsch & Maniatis, "Molecular Cloning: A Laboratory Manual," Second Edition (1989) Cold Spring Harbor Laboratory Press, Cold Spring Harbor, N.Y. (herein "Sambrook et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The gene encoding the fusion protein will be part of an expression construct. The gene is positioned to be under transcriptional and translational regulatory regions functional in the cellular host. The regulatory region may include an enhancer, which may provide such advantages as limiting the type of cell in which the fusion protein is expressed, requiring specific conditions for expression, naturally being expressed with the protein of interest, and the like. In many instances, the regulatory regions may be the native regulatory regions of the gene encoding the protein of interest, where the fusion protein may replace the native gene, particularly where the fusion protein is functional as the native protein, may be in addition to the native protein, either integrated in the host cell genome or non-integrated, e.g. on an extrachromosomal element.

In an initial phase of the development of an assay, one may wish to have a second marker as part of the fusion protein. The second marker may be any marker that allows for detection independently of the ED. Such markers include antigenic epitopes that can be recognized by a labeled antibody, polyhistidine that can be detected with a nickel reagent, etc.

In those cells in which the native protein is present and expressed, the fusion protein will be competing with the native protein for transcription factors for expression. The site of the gene in an extrachromosomal element or in the chromosome may vary as to transcription level. Therefore, in many instances, the transcriptional initiation region will be selected to be operative in the cellular host, but may be from a virus or other source that will not significantly compete with the native transcriptional regulatory regions or may be associated with a different gene from the gene for the protein of interest, which gene will not interfere significantly with the transcription of the fusion protein.

It should be understood that the site of integration of the expression construct will affect the efficiency of transcription and, therefore, expression of the fusion protein. One may optimize the efficiency of expression by selecting for cells having a high rate of transcription, one can modify the expression construct by having the expression construct joined to a gene that can be amplified and coamplifies the expression construct, e.g. DHFR in the presence of methotrexate, or one may use homologous recombination to ensure that the site of integration provides for efficient transcription. In this way one may overwhelm the expression of the naturally occurring protein, so that the fusion protein is the major determinant of the function of the target protein and its modification in the cell. By inserting an insertion element, such as Cre-Lox at a site of efficient transcription, one can direct the expression construct to the same site. In any event, one will usually compare the enzyme activity from cells in a predetermined environment to cells in the environment being evaluated. One would still retain the naturally occurring protein, which can be analyzed using labeled antibodies to compare the modifications of the naturally occurring protein with the fusion protein.

Depending upon the purpose of the analysis and whether in vitro or in vivo, one may analyze a substantially homogeneous cellular composition or a heterogeneous cellular composition. That is, one could have a mixture of cells that are free of the fusion protein and contain the fusion protein. As indicated above, one may wish to analyze the modifications of the naturally occurring target protein for comparison with the fusion protein. Once one has established the relevance of the fusion protein to the effects on the naturally occurring protein, the comparison need not be repeated.

There are a large number of commercially available transcriptional regulatory regions that may be used and the particular selection will generally not be crucial to the success of the subject invention. Also, the manner in which the fusion gene construct is introduced into the host cell will vary with the purpose for which the fusion gene is being used. The introduction of the construct may be performed in vitro or in vivo and will include situations where cells transformed in culture are then introduced into the mammalian host. The transcriptional regulatory region may be constitutive or inducible. In the former case, one can have a steady state concentration of the fusion protein in the host, while in the latter case one can provide going from the substantially total absence (there is the possibility of leakage) to an increasing amount of the fusion protein until a steady state is reached. With inducible transcription, one can cycle the cell from a state where the fusion protein is absent to a state where the steady state concentration of the fusion protein is present.

Vectors for introduction of the construct include an attenuated or defective DNA virus, such as but not limited to, herpes simplex virus (HSV), papillomavirus, Epstein Barr virus (EBV), adenovirus, adeno-associated virus (AAV), and the like. Defective viruses, appropriately packaged, which entirely or almost entirely lack viral genes, are preferred. Defective virus is not infective after introduction into a cell. Use of defective viral vectors, particularly tropic for particular cell types, allows for administration to cells in a specific, localized area, without concern that the vector can infect other cells. Thus, a particular locus can be specifically targeted with the vector. Specific viral vectors include: a defective herpes virus 1 (HSV1) vector (Kaplitt et al., 1991, Molec. Cell. Neurosci. 2:320-330); an attenuated adenovirus vector, such as the vector described by Stratford-Perricaudet et al. (1992, J. Clin. Invest. 90:626-630 a defective adeno-associated virus vector (Samulski et al., 1987, J. Virol. 61:3096-3101; Samulski et al., 1989, J. Virol. 63:3822-3828).

The vector may be introduced in vitro and in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection. (Felgner, et. al., 1987, Proc. Natl. Acad. Sci. U.S.A. 84:7413-7417; see Mackey, et al., 1988, Proc. Natl. Acad. Sci. U.S.A. 85:8027-8031). The use of cationic lipids may promote encapsulation of negatively charged nucleic acids, and also promote fusion with negatively charged cell membranes (Felgner and Ringold, 1989, Science 337:387-388). Lipofection into the nervous system in vivo has recently been achieved (Holt, et. al., 1990, Neuron 4:203-214). The use of lipofection to introduce exogenous genes into the nervous system in vivo has certain practical advantages. Lipids may be chemically coupled to other molecules for the purpose of targeting (see Mackey, et. al., 1988, supra). Targeted peptides or non-peptide molecules can be coupled to liposomes chemically.

It is also possible to introduce the vector in vitro and in vivo as a naked DNA plasmid, using calcium phosphate precipitation or other known agent. Alternatively, the vector containing the gene encoding the fusion protein can be introduced via a DNA vector transporter (see, e.g., Wu et al., 1992, J. Biol. Chem. 267:963-967; Wu and Wu, 1988, J. Biol. Chem. 263: 14621-14624; Hartmut et al., Canadian Patent Application No. 2,012,311, filed Mar. 15, 1990).

Vectors are introduced into the desired host cells in vitro by methods known in the art, e.g., transfection, electroporation, microinjection, transduction, cell fusion, DEAE dextran, calcium phosphate precipitation, lipofection (lysosome fusion), use of a gene gun, using a viral vector, with a DNA vector transporter, and the like.

Advantages associated with in vivo introduction of the fusion protein expression construct are that one has the expression of the fusion protein in a natural setting where the factors normally associated with the status of the cell are present. For example, if one were interested in knowing how a drug acted on a cell type in relation to the protein of interest, by testing the drug in vivo, one is able to determine the response of the protein of interest under natural conditions. Using experimental laboratory animals, one could isolate cells from the organ or site of interest and have a mixture of cells transformed with the fusion protein construct and untransformed cells. As indicated previously, one could have a comparison of the naturally occurring target protein and the fusion protein. For specific expression of the fusion protein in a target host cell, one could use a transcriptional regulatory region that is active in the target host cell and not active in other cells, e.g. prostate specific antigen transcriptional regulatory region for use with prostate cancer cells.

One may use promoters that are active for a short time, such as viral promoters for early genes, for example, the human cytomegalovirus (CMV) immediate early promoter. Other viral promoters include but are not limited to strong promoters, such as cytomegaloviral promoters (CMV), SR alpha (Takebe et al., Mole. Cell. Biol. 8:466 (1988)), SV40 promoters, respiratory syncytial viral promoters (RSV), thymine kinase (TK), beta.-globin, etc. Alternatively, an inducible promoter can be used.

A large number of promoters have found use in various situations, for various purposes and for various hosts. Many promoters are commercially available today. Expression of the fusion protein may be controlled by any promoter/enhancer element known in the art, but these regulatory elements must be functional in the host or host cell selected for expression. Promoters which may be used to control fusion gene expression include, but are not limited to, the SV40 early promoter region (Benoist and Chambon, 1981, Nature 290: 304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315: 115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58), alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94), myelin basic protein gene control region which is active in oligodendrocyte cells in the brain (Readhead et al., 1987; Cell 48:703-712), myosin light chain-2 gene control region which is active in skeletal muscle (Sani, 1985, Nature 314:283-286), prostate specific antigen control region, which is active in prostate cells (U.S. Pat. Nos. 6,197,293 and 6,136,792), and gonadotropic releasing hormone gene control region which is active in the hypothalamus (Mason et al., 1986, Science 234: 1372-1378). Alternatively, expression of the fusion protein gene can be under control of an inducible promoter, such as metallothionein promoter, which is induced by exposure to heavy metals or a promoter responsive to tetracycline (tet-responsive promoter). For control of the gene transfected into certain brain cells, a glucocorticoid inducible promoter can be used, since glucocorticoids can cross the blood-brain barrier. Alternatively, an estrogen inducible promoter, which would be active in the hypothalamus and other areas responsive to estrogen, can be used. The present invention contemplates the use of any promoter inducible by a pharmacologic agent that can cross the membrane and for neuronal cells, the blood-brain barrier and influence transcription.

Vectors containing DNA encoding the following proteins, for example, have been deposited with the American Type Culture Collection (ATCC) of Rockville, Md.: Factor VIII (pSP64-VIII, ATCC No. 39812); a Factor VIII analog, "LA", lacking 581 amino acids (pDGR-2, ATCC No. 53100); t-PA and analogs thereof (see co-pending U.S. application Ser. No. 882,051); VWF (pMT2-VWF, ATCC No. 67122); EPO (pRK1-4, ATCC No. 39940; pdBPVMMTneo 342-12 (BPV-type vector) ATCC No. 37224); and GM-CSF (pCSF-1, ATCC No. 39754).

The vector will include the fusion gene under the transcriptional and translational control of a promoter, usually a promoter/enhancer region, optionally a replication initiation region to be replication competent, a marker for selection, as described above, and may include additional features, such as restriction sites, PCR initiation sites, an expression construct providing constitutive or inducible expression of EA, or the like. As described above, there are numerous vectors available providing for numerous different approaches for the expression of the fusion protein in a host.

Of the protein categories of interest, transcription factors, inhibitors, regulatory factors, enzymes, membrane proteins, structural proteins, and proteins complexing with any of these proteins, are of interest. Specific proteins include enzymes, such as the hydrolases exemplified by amide cleaving peptidases, such as caspases, thrombin, plasminogen, tissue plasminogen activator, cathepsins, dipeptidyl peptidases, prostate specific antigen, elastase, collagenase, exopeptidases, endopeptidases, aminopeptidase, metalloproteinases, including both the serine/threonine proteases and the tyrosine proteases; hydrolases such as acetylcholinesterase, saccharidases, lipases, acylases, ATP cyclohydrolase, cerebrosidases, ATPase, sphingomyelinases, phosphatases, phosphodiesterases, nucleases, both endo- and exonucleases; oxidoreductases, such as the cytochrome proteins, the dehydrogenases, such as NAD dependent dehydrogenases, xanthine dehyrogenase, dihydroorotate dehydrogenase, aldehyde and alcohol dehydrogenase, aromatase; the reductases, such as aldose reductase, HMG-CoA reductase, trypanothione reductase, etc., and other oxidoreductases, such as peroxidases, such as myeloperoxidase, glutathione peroxidase, etc., oxidases, such as monoamine oxidase, myeloperoxidases, and other enzymes within the class, such as NO synthase, thioredoxin reductase, dopamine β-hydroxylase, superoxide dismutase, nox-1 oxygenase, etc.; and other enzymes of other classes, such as the transaminase, GABA transaminase, the synthases, β-ketoacyl carrier protein synthase, thymidylate synthase, synthatases, such as the amino acid tRNA synthatase, transferases, such as enol-pyruvyl transferase, glycinamide ribonucleotide transformylase, COX-1 and -2, adenosine deaminase.

Kinases are of great significance, such as tyrosine kinases, the MAP kinases, the cyclin dependent kinases, GTP kinases, ser/thr kinases, Chk1 and 2, etc.

Also of interest are enzyme inhibitors, such as $\alpha_1$-antitrypsin, antithrombin, cyclophilin inhibitors, proteasome inhibitors, etc.

Other proteins of interest are the oncogenes, such as Src, Ras, Neu, Erb, Fos, Kit, Jun, Myc, Myb, Abl, Bcl, etc. Cytokines, such as the interferons, α-γ, interleukins, 1-19, and integrins, adhesins, TNF, receptors, hormones, colony stimulating factors, growth factors, such as epidermal growth factor, fibroblast growth factor, etc., bone morphogenetic proteins, developmental proteins, such as the Hox proteins, or other proteins binding to or regulating proteins binding to homeoboxes, e.g. the hedgehog proteins, basement membrane proteins, heat shock proteins, proteins containing Krupple and Kringle structures chaperonins, calcium associated proteins, e.g. calmodulin, calcineurin, etc., membrane channels, transporter proteins, etc.

Also of interest are the proteins associated with proliferation, such as the cyclins, cyclin dependent kinases, p53, RB, etc.

Neuronal proteins, such as β-amyloid, TNF, prion, APP, transporters, e.g. dopamine transporter, receptors, such as NMDA receptors, AMDA receptors, dopamine receptors, channels, etc.

Another class of proteins is the transcription factors and their inhibitors or regulatory proteins, such as Adr Ace, Amt, AP, Atf, Att, Baf, Brn, Btf, C Ebp, C Jun, C Ets, CREB, CF, Chop, DP, E2F, Elk, Gata, Hnf, Iii A-H, Irf, NY Y, Otf, NFκB, NF-AT, Oct-1, Pea, Pit, PU, S, SP, Stat, Tef, TFIII, TFIIII, Ubf and Usf, while the inhibitors include Erk, IκB, LIF, Smad, RANTES, Tdg, etc., as well as other proteins associated with pathways that induce transcription factor synthesis, activation or inhibition.

Another class of proteins that are of interest are the surface membrane proteins, where many of such proteins are receptors, such as G protein coupled receptors, hormone receptors, interleukin receptors, steroid receptors, transporters, etc. These receptors include insulin receptor, glucose transporter, IL-2, 4, etc. receptor, CRXC4, PPAR, etc. Also, the MHC proteins can be of interest.

In some instances, housekeeping proteins will be of interest, such as the proteins involved in the tricarboxylic acid cycle, the Krebs cycle, glycogenesis, etc.

As indicated previously, the genes of each of these proteins may be manipulated in numerous ways to fuse ED with the protein while maintaining the biological activity of the protein and ED.

Various pathways will be of interest associated with the different proteins. Thus, pathways involving signal transduction as a result of ligand binding to a surface membrane protein receptor, vesicle formation and transport, multistage synthesis of cellular components, proteasomes, peroxisomes, spindle formation, tubulin assemblage, processing of ingested compounds, e.g. toxins, drugs, etc.

One can also use the subject system to measure the effectiveness of an antisense or RNAi present in a cell. By measuring the amount of fusion protein that is expressed and present in the cell, the efficiency of the antisense or RNAi in preventing expression can be measured. In addition, one can determine the effect of the reduction of the expression of one protein on another protein, where the other protein is the fusion protein. For example, where one is interested in the effect of the absence of expression on a pathway, where the fusion protein is downstream from the inhibited protein, one can determine whether there are alternative pathways for the expression of the fusion protein. Alternatively, one may investigate the effect of a change in the transduction of a signal in one pathway on an alternative pathway involving the fusion protein or on the modification of the fusion protein. The combination of inhibition of one protein while measuring the expression level or modification of another protein is a powerful tool in understanding intracellular activity, the interactions of different pathways and the effect of a change in environment on such intracellular activity.

The cells comprising the subject constructs may be used to identify proteins associated with a pathway of interest, the effect of a change in environment, such as the presence of a drug or drug candidate, on the presence of the protein of interest in the cell, changes in the regulation of expression, the effect of inhibiting expression of a protein, the regulation by a receptor of a cellular pathway and to that extent, compounds that affect the transduction of a signal by the receptor, the activation or deactivation of cellular pathways that affect the complex formation or degradation of the fusion protein, expression level of a protein, related to the rates of formation and degradation, etc.

Secreted proteins can be determined while they are intracellular. Prior to being transported from the Golgi to the surface membrane, a number of steps must occur and one can determine the number of such molecules in the cell and whether they are complexed with other proteins, e.g. docking protein.

The host cells will be selected to provide the necessary transcription factors for expression of the fusion protein and the other components for the purposes of the determination. The host cells will also be selected toward providing an environment resembling the environment being simulated. In many cases primary cells may be employed, both those maintained in culture and obtained directly from a patient. However, in many other cases, established cell lines will be used, since the cell lines can provide the desired environment and allow for direct comparisons between studies, which comparisons may not be available when using primary cell lines from patients.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Embryonic cells may find use, as well as stem cells, e.g. hematopoietic stem cells, neuronal stem cells, muscle stem cells, etc. Candidate cells need not be genotypically deficient in a selection gene so long as the selection gene is dominantly acting. The host cells preferably will be established mammalian cell lines. For stable integration of vector DNA into chromosomal DNA, and for subsequent amplification of the integrated vector DNA, both by conventional methods, CHO (Chinese Hamster Ovary) cells are convenient. Alternatively, vector DNA may include all or part of the bovine papilloma virus genome (Lusky et al., 1984, Cell 36:391-401) and be carried in cell lines such as C127 mouse cells as a stable episomal element. Other usable mammalian cell lines include HeLa, COS-1 monkey cells, melanoma cell lines such as Bowes cells, mouse L-929 cells, mouse mammary tumor cells, 3T3 lines derived from Swiss, Balb-c or NIH mice, BHK or HAK hamster cell lines and the like.

Cell lines may be modified by knocking out specific genes, introducing specific genes, enhancing or diminishing the expression of a protein or the like. The modification may be transient, as in the case of introduction of antisense DNA, RNAi, or dsRNA or may be permanent, by deleting a gene, introducing a gene encoding the antisense mRNA of the target protein, adding a dominant recessive gene, or the like. Research animals may be employed of various strains, where the strains are a result of naturally occurring mutations and breeding or using genetic modifications of embryonic or other cells with a resulting genetically modified host, which may be vertebrate, e.g. mammalian, fish, insect, or the like, or non-vertebrate, e.g. nematode, etc. Knock-out mice are extensively described in the literature. One may use the intact host, tissue from the intact host or cells from the intact host for the purposes of this invention. Illustrative of the development of knockout and knockin mice are Nozawa, et al., Transplantation 2001, 72:147-55; Ferreira, et al., Blood 2001 98:525-32; Kotani, et al., Biochem. J. 2001, 357:827-34; Zhou, et al., Int. J. Radiat. Biol. 2001, 77:763-72; and Chang, et al., Mol. Cell. Endocrinol. 2001, 180:39-46, and references cited therein, to provide only a few of the large number of publications concerning genetically modified mice. In addition one may use hybridomas, where a first cell having the desired gene(s) is fused with an immortalized cell under conditions where the chromosomes from the first cell are stably maintained. The gene(s) could be transcription factors, proteins of interest, e.g. human proteins in a non-human host cell, or provide for enhanced expression of a protein.

The ED of β-galactosidase is extensively described in the patent literature. U.S. Pat. Nos. 4,378,428; 4,708,929; 5,037,735; 5,106,950; 5,362,625; 5,464,747; 5,604,091; 5,643,734; and PCT application nos. WO96/19732; and WO98/06648 describe assays using complementation of enzyme fragments. The ED will generally be of at least about 35 amino acids, usually at least about 37 amino acids, frequently at least about 40 amino acids, and usually not exceed 100 amino acids, more usually not exceed 75 amino acids. The upper limit is defined by the effect of the size of the ED on the performance and purpose of the determination, the effect on the complementation with the EA, the inconvenience of a larger construct, and the like. The minimum size that can be used must provide a signal that is observable with the products of the cellular events and that can be determined with reasonable sensitivity. The examples in the Experimental section will provide guidelines as to how to obtain a fusion protein with the desired sensitivity for the assay.

The state of all intracellular proteins can be determined in accordance with this invention to the extent that the fusion protein can serve as a surrogate for a protein of interest, since all proteins will be subject to some modification, e.g. degradation. For the most part, the proteins of interest will be associated with a health function, such as the effect of an infectious disease, genetic defect, mutation, response to a drug, neoplasia, inflammatory response, etc. Thus, the change in the migration rate of the fusion protein will be relevant to a physiological function, usually associated with the diagnosis and treatment of mammalian hosts, although there may be other purposes, such as investigation of pathways.

A number of substrates for β-galactosidase are known, where the product is fluorescent. The common substrates are β-D-galactopyranosyl phenols, such as fluorescein, mono- and di-susbtituted, o-nitrophenyl-β-D-galactoside, β-methylumbelliferyl-β-D-galactoside, X-gal, resorufin-β-D-galactoside, commercially available dioxetanes, e.g. Galacto-Light Plus® kits (chemiluminescence) and chlorophenol red. The di-β-D-galactopyianosylfluorescein, and chlorophenol red-β-D-galactopyranoside, or analogous substrates, particularly where the product is inhibited from leaking from the cell, may be used as intracellular markers.

During the determination, the cells are maintained in a viable state, where the cells may be dividing or not dividing. The viable state may be referred to as growing.

The simplest procedure to describe is the use of cells in culture and analysis of the lysate. In this case, the cells are grown in culture. The fusion protein and other constructs, as appropriate, may be present in the cell integrated into the genome or may be added transiently by the various methods for introducing DNA into a cell for functional translation. The cells may be in culture or in vivo. These methods are amply exemplified in the literature, as previously described. By employing a marker with the fusion protein for selection of cells comprising the construct, such as antibiotic resistance, development of a detectable signal, etc., cells in culture comprising the fusion protein can be separated from cells in which the construct is absent. Once the fusion protein is being expressed, the environment of the cells may be modified, if desired. Candidate compounds may be added, ligand for receptors, surface membrane or nuclear, or the two of these may be added in combination, changes in the culture medium may be created, other cells may be added for secretion of factors or binding to the transformed cells, viruses may be added, or the like. Given sufficient time for the environment to take effect and/or taking aliquots of the culture at different time intervals, the cells may be lysed with a lysis cocktail, the lysis cocktail subjected to electrophoretic separation and Western blotting followed by addition of EA and enzyme substrate and the signal from the product read. One can then relate this result to the amount of fusion protein present, particularly by using standards where the lysate is spiked with different amounts of the fusion protein and the amount of active fusion protein determined, as well as modification products of the fusion protein, using standards for the modified product. One would then have a graph relating signal to amount of each of the products of the fusion protein in the lysate.

Where the cells are in a viable host, usually the cells or tissue from the host will be harvested and lysed, so that the methodology used for the culture will be the same. If desired, selection of cells having the construct can be achieved by having an antibiotic resistance gene as part of the construct, so that cells can be selected using the antibiotic to avoid dilution of the sample by cells lacking the construct.

For convenience, kits can be provided that may include all or some of the major components of the assays. For example, a kit may include an expression construct, by itself or as part of a vector, e.g. plasmid, virus, usually attenuated, where the expression construct may include a marker, a gene encoding a protein for integration, a replication initiation site, and the like. The construct may be extracellular or provided integrated into the genome of a cell. In addition to the expression construct, the kit may include EA, substrate for β-galactosidase, one or more cell lines or primary cells, a graph of response in relation to the amount of ED present, buffers, separation gels, membranes for the Western blotting, filter paper, etc. In some instances cells may be engineered to provide a desired environment, such as high levels of expression of a protein involved in a pathway of interest, such as surface membrane receptors, GPCRs, nuclear receptors, e.g. steroid receptors, transcription factors, etc. or may have been mutated, so as to have reduced levels of expression affecting the expression of the fusion protein and one is interested in enhancing the level of expression.

The system is initially used to determine whether the gene to be inserted results in a fusion protein that is biologically active to serve as a surrogate for the natural protein, either providing the activity of the natural protein or responding to modifications in a parallel way to the natural protein. The activity of the fusion protein may be determined by using host cells in which the expression of the natural protein does not occur. This may be as a result of cells in which both copies of the natural protein have been knocked-out; where antisense RNA or RNAi is added to the host cell that inhibits the natural protein but not the fusion protein, e.g. as to the non-coded 3'-region or includes the 5'-methionine codon; where antisense RNA or RNAi inhibits a transcription factor necessary for expression of the natural protein, where the fusion protein has a different transcriptional regulatory region.

In developing the use of the fusion proteins, systems can be devised that allow for screening of genetic constructs for their application to the desired investigation. The user of the system introduces the gene of interest into the genetic construct provided in the system. By having a multiple cloning site, the gene is manipulated so as to be inserted into the multiple cloning site in the correct orientation and in reading frame with the ED sequence. Usually, there will be a linker of not more than 3 codons, preferably not more than about 2 codons, as a result of the nucleotides present in the multiple cloning site remaining between the ED sequence and the gene of interest. As indicated, the vector that is provided may include the transcriptional and/or translational termination sequences, a polyadenylation sequence, or other sequence that encodes a function, e.g. farnesylation, geranylation, etc. Once the fusion protein construct has been completed, the construct may then be introduced into the host cell.

The steps employed by the subject invention comprise: (1) preparing the fusion protein gene and expression construct by insertion of the gene of interest into a multiple cloning site of a genetic construct provided as part of the system; (2) introducing the expression construct comprising the fusion protein into a selected cell host, provided by the system or selected by the user; (3) incubating the transformed cell host under conditions that permit expression and cell viability; (4) lysing the cells; (5) separating the proteins using gel electrophoresis; (6) transfer of the separated protein bands by Western blotting; (7) adding EA and substrate, usually in two stages to the gel; and (7) identifying the bands on the membrane that are developed by the detectable product of the substrate. When adding EA to the gel, usually a large excess of EA to ED will be added, usually at least about two-fold excess, frequently at least about five-fold excess, and the excess may be 20-fold or greater.

Using the various components described above for use in this invention, the system can be employed to determine whether the host and expression construct are compatible, whether transient expression, extended expression, or permanent expression should be employed, whether primary, immortal or cells of intermediate nature should be employed, and the response to known agents. In this way, one can optimize the particular system to provide for increased sensitivity to particular agents.

The system can be used with a data accumulation and storage capability, where the data derived from the system is collected, analyzed and compared to other determinations. In this way, data can be accumulated of the effect of various agents on the history of the fusion protein, so that one can measure how the genetically modified cells respond to the addition of individual or combinations of candidate drugs, variations in rate of change, affect on different pathways and the like. By having a database of known responses to compounds that have established effects, new candidates can be compared to such results for evaluation of their anticipated physiological effects. Not only can one study the effect of such candidates on targets, but also the side effects resulting from the presence of such targets in the media.

As indicated, the subject method can be used in a variety of situations to great effect, since the ED is small enough to allow for functioning of the protein of interest as a fusion protein with ED, while allowing for ED to complex with EA to provide a functional enzyme.

The following examples are offered by way of illustration and not by way of limitation.

EXPERIMENTAL

The first experimental example provides a comparison of EAstern and Western blot methods for detecting specific proteins present in whole-cell lysates. The specific proteins in this experiment were fusion proteins tagged with both Pro-Label (ED; see WO 03/021265, see SEQ ID NO:1) and the c-myc epitope tag, which allow for EFC and antibody detection methods, respectively. The proteins were expressed from plasmids in transiently transfected CHO-K1 cells. Plasmid pPL-myc-βarr2 expresses a PL-myc-β-arrestin2 fusion protein from the CMV promoter and was constructed in two steps. First, a myc-βarr2 DNA fragment was obtained by PCR amplification from a human β-arrestin2 cDNA clone (MGC: 3754, IMAGE:3028154, Invitrogen) using a forward primer that introduced a BglII site and nucleotides encoding the c-myc epitope tag (amino acids EQKLISEEDL; SEQ ID NO: 5) in place of the βarr2 start codon and a reverse primer that introduced an EcoRI site downstream of the βarr2 stop codon. Second, the amplified DNA was digested with BglII and EcoRI and inserted into the vector pCMV-PL-N1, which had been prepared by digestion with the same enzymes. Plasmid pbarr2-myc-PL expresses a β-arrestin2-myc-PL fusion protein from the CMV promoter and was constructed in a similar manner. First, a βarr2-myc DNA fragment was obtained by PCR amplification from the β-arrestin2 cDNA using a forward primer that introduced a BglII site upstream of the βarr2 start codon and a reverse primer that introduced nucleotides encoding the c-myc epitope tag in place of the βarr2 stop codon followed by an EcoRI site. Second, the amplified DNA was digested with BglII and EcoRI and inserted into vector pCMV-PL-C1, which had been prepared by digestion with the same enzymes. The DNA sequences of the cloning vectors pCMV-PL-N1 and pCMV-PL-C1 are shown in SEQ ID NO:1 and SEQ ID NO:2, respectively. Translation of the PL-myc-βarr2 and βarr2-myc-PL fusion proteins are shown in SEQ ID NO:3 and SEQ ID NO:4, respectively. The third plasmid used in this experiment was pEGFP-C1 (BD Clontech), which expresses untagged green fluorescent protein from the CMV promoter and served as a negative control.

Protein blots were prepared from cell lysates using standard technique. A 10 cm dish of CHO-K1 cells that had been grown to confluency was trypsinized and seeded into three fresh 10 cm dishes at one-tenth dilution. The cells were then transiently transfected with 5 μg/10 cm dish of the three plasmids described above using the FuGENE 6 reagent (Roche). Two-days after transfection, the growth medium was removed and the cells were washed once with 10 ml PBS. The cells were then lysed by adding 1 ml of ice-cold CLB (Cell Lysis Buffer: 0.5% CHAPS in PBS) and scraping cell debris from the plate surface. The lysates were transferred to microtubes on ice and vortexed periodically over a 30 min period. Samples for gel electrophoresis were prepared by combining 0.65 vol cell lysate/0.25 vol 4×LDS buffer/0.1 vol 10× reducing agent (the later two components obtained from Invitrogen), followed by heating at 70° C. for 10 min. Electrophoresis of protein samples on denaturing NuPAGE 4-12% Bis-Tris gels and transfer to nitrocellulose membranes were carried out according to the manufacturer's instructions (Invitrogen). Several replica blots were prepared at the same time.

EAstern blot detection of PL-tagged proteins on one blot was carried out using the chromogenic β-galactosidase substrate X-Gal. Following transfer from the gel, the blot was equilibrated in EACB (EA Core Buffer, DiscoveRx) at room temp. for 5 min, followed by incubating with EA Reagent (~0.14 ml/cm² membrane, DiscoveRx) at 37° C. for 1 hr.

Without washing, the membrane was placed in a Petri dish, protein-side up, atop two sheets of 3 MM blotting paper saturated with substrate solution (0.33 mg/ml X-Gal, 3.5 mM β-mercaptoethanol in EACB). The dish was sealed with parafilm and placed at room temperature to allow color development. Representative photographs of the EAstern blot at various times of development are shown in the upper panels of FIG. 1. Specific signal continued to develop over the course of several days. There was no detectable non-specific signal in the pEGFP-C1 control lane, nor was there background staining of the blot itself (FIG. 1).

Western blotting was performed to detect myc-epitope tagged proteins. Blots were first incubated with shaking for 30 min in blocking buffer (TTBS/3% nonfat milk powder; TTBS is 100 mM Tris pH 7.5, 0.9% w/v NaCl, 0.1% v/v Tween 20). The blots were then incubated for 45 min with antibodies diluted in blocking buffer as follows: anti-myc mouse monoclonal (clone 9E10, Abcam Ltd., Cat. No. ab32), 1:5000; anti-myc rabbit polyclonal (Abcam Ltd., Cat. No. ab9106), 1:1000. The blots were washed four times for 5 min in TTBS before incubating for 30 min with the corresponding alkaline-phosphatase conjugated secondary antibodies (Applied Biosystems Cat. Nos. AC32ML and AC31RL) diluted 1:10,000 (v/v) in TTBS/3% NFM. The membranes were washed as above, followed by a final wash in CSB (CDP-Star Buffer: 100 mM 2-amino-2-methyl-1-propanol pH 9.5, 0.8 mM $MgCl_2$). For development, membranes were incubated at 37° C. for 10 min in substrate solution (50 µM CDP-Star, 0.5 mg/ml Sapphire II, both from Applied Biosystems, diluted in CSB), sandwiched between clear plastic sheets, and their luminescence detected with a CCD camera using various exposure times. Representative exposures for the anti-myc monoclonal and polyclonal Western blots are shown in the lower panels of FIG. 1.

The second experimental example illustrates the sensitivity of the EAstern blot method by following the regulated degradation of a PL-tagged cellular protein, IκB-PL. In most cells, the binding of inhibitor protein IκB holds the transcription factor NF-κB in an inactive form. Stimulation of cells with cytokines, such as TNF-α, activates a pathway that leads to phosphorylation, ubiquitination, and subsequent degradation of IκB, which in turn leads to the release and activation of NF-κB. The regulated degradation of IκB is thus an indicator for NF-κB pathway activation.

Figure 2:
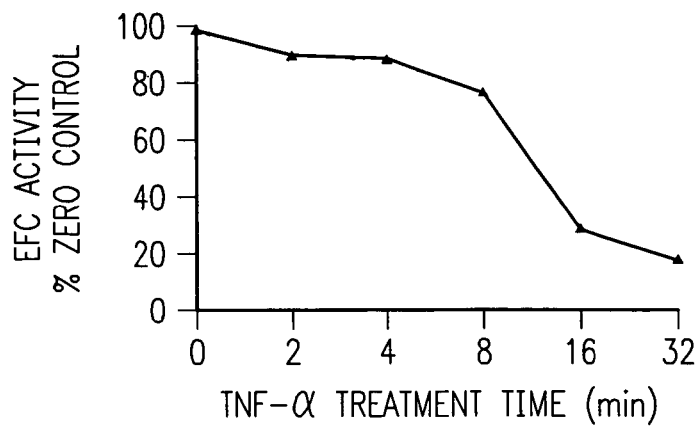
FIG. 2 is a graph showing the amount of Iκβ-PL protein present in lysates after HeLa Iκβ-PL stable cells were treated with TNF-α for the indicated time periods. EFC values are expressed as percentages of untreated control cells ("0" time point)

Cell lysate samples for EAstern blot analysis were prepared from a HeLa/IκB-PL stable cell line (WO 03/021265, filed Aug. 27, 2002) that was cultured and stimulated with TNF-α for increasing time periods. A fraction of each lysate was tested by homogenous EFC assay to confirm the TNF-α induced, time-dependent degradation of IκB-PL signal (FIG. 2). Another fraction of each was used for gel electrophoresis and transfer to PVDF blots as described above. To detect IκB-PL, the EAstern blot protocol was adapted for use with the chemiluminescent substrate Beta-Glo (Promega Corp., Cat. No. E4720). In particular, after incubating with EA Reagent, the blot was incubated at RT for 10 min in a solution of Beta-Glo:EACB (1:1, v/v), sandwiched between clear plastic sheets, and then its luminescence detected with a CCD camera. To control for variations in sample preparation, a replica blot was probed with an anti-actin monoclonal antibody as described above for Western blotting (Abcam Ltd., Cat. No. ab6276); actin levels are not significantly affected by TNF-α.

Figure 3:
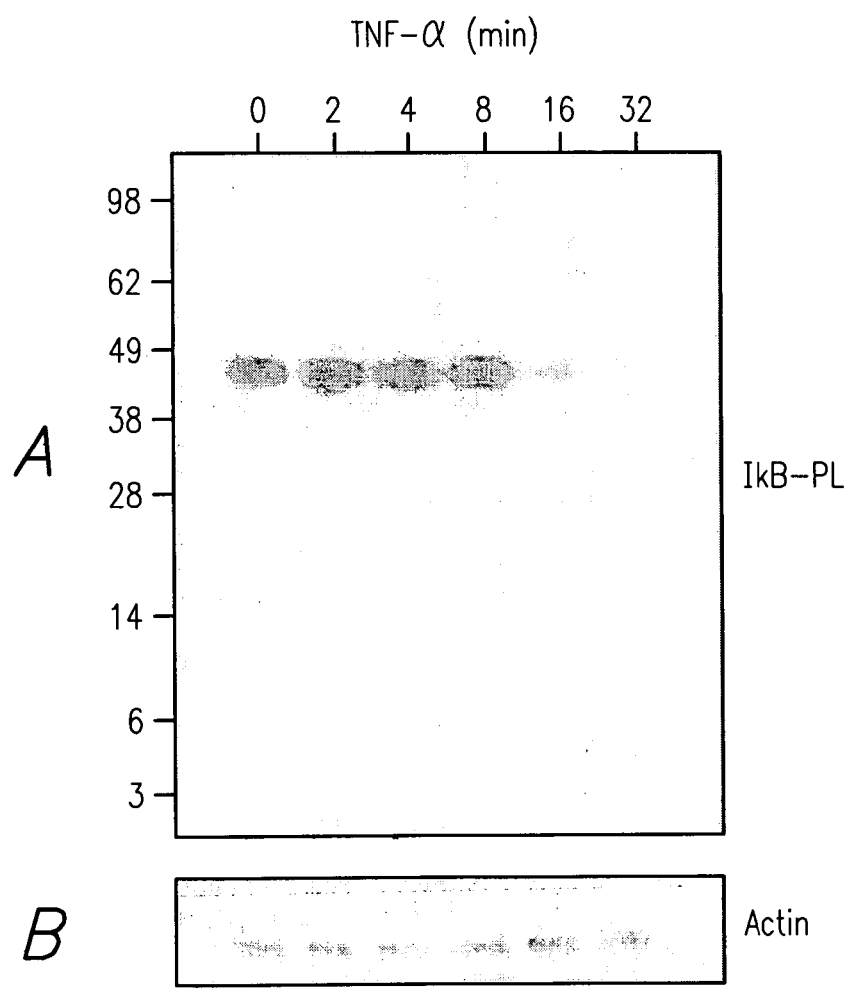
FIG. 3 shows EAstern blot detection (upper panel, A) of Iκβ-PL using the chemiluminescent substrate Beta-Glo and a 3 min CCD camera exposure. Molecular weight marker sizes (kD) are indicated on the left. The anti-actin Western blot (lower panel, B) serves as a loading control. Samples are the same as those described in FIG. 2.
Figure 4:
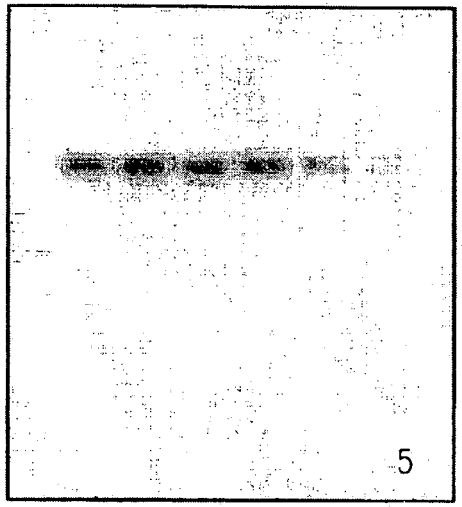
FIG. 4 shows increased CCD camera exposure times (in minutes, lower-right corner of each panel, 4A, 5 min., 4B 10 min., 4C 15 min., 4D 30 min.) of the EAstern blot shown in FIG. 3. The asterisk (*) in D marks the region on the blots where high MW bands appeared with longer exposure times.
Figure 4:
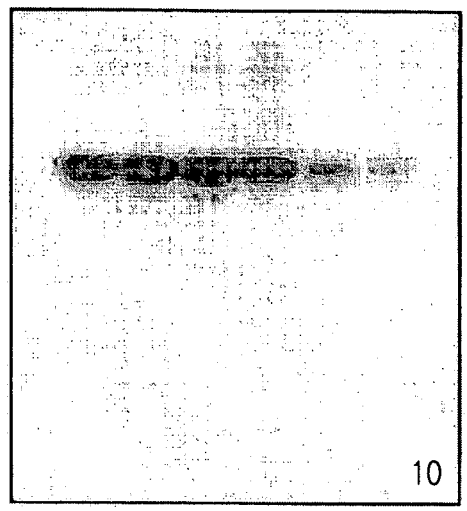
Figure 4:
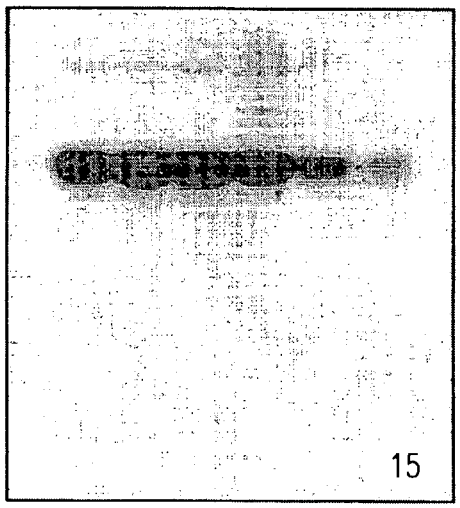
Figure 4:
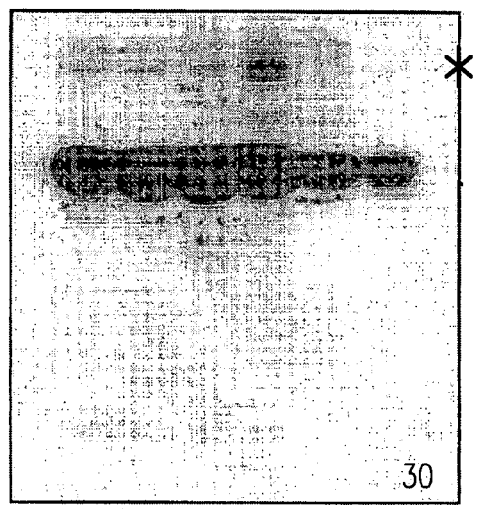

A thirty minute exposure of the EAstern blot (FIG. 4D) revealed in the lysates a single band that migrated at the predicted molecular weight of IκB-PL (42.1 kDal) and whose abundance throughout the TNF-α time course paralleled the EFC signal in the homogenous assay (compare FIGS. 3 and 4). Increased sensitivity was obtained with increased CCD camera exposure time (FIG. 4). Several high molecular weight bands appeared at the longer exposure times (see 10, 15, and 30 min exposures in FIG. 4) that appear to represent IκB-PL modified by poly-ubiquitination, based on the timing of their appearance relative to TNF-α stimulation and IκB-PL degradation. Poly-ubiquitination is a known post-translational modification that occurs in response to cytokine stimulation and is a prerequisite for IκB degradation. These bands in similar experiments using the Western blot method with several commercial preparations of anti-IκB antibodies were not previously observed by us. Thus, the high specificity and sensitivity of the EAstern blot technique allows for detection levels that exceed those of traditional Western blotting.

In the following, a series of experiments were performed varying the parameters of the EAstern protocol in order to identify conditions that would yield optimal results.

For the next series of experiments generation of cell lysates, protein blot transfer and EAstern analysis of PL-tagged proteins was carried out as described above with the following modifications. First, transfections of HeLa cells with different ProLabel expressing plasmid DNAs (0.5 µg) and/or siRNAs to STAT1 (GenBank accession # NM_032612), Cyclin D1(GenBank accession # NM_003210), p53 (GenBank accession # NM_001641) and IκB (GenBank accession # NM_010546) were done in 12 well plates. Second, transfections using Lipofectamine 2000 (Invitrogen), were allowed to go for 16 hours after which the cells were treated with trypsin and collected by centrifugation in a microfuge tube. Third, the cell pellet was then washed 1× with PBS, centrifuged again and resuspended in 400 mL of DiscoveRx cell lysis buffer (0.5% CHAPS in PBS+1× COMPLETE protease inhibitor cocktail {Roche, catalog # 1873580}. The cells were lysed by continuous vortexing at 37° C. for 30 minutes. Preparation of samples for SDS-PAGE was performed as described above. Samples were run on a NuPAGE 4-12% Bis-Tris gel under denaturing conditions and transferred to nitrocellulose membrane according to the protocol outlined in the manufacturer's instructions (Invitrogen). The membrane was transferred to a plastic dish and washed 2 times for 5 minutes in EA core buffer (DiscoveRx). The blot was then incubated with 4 mL of EA solution (DiscoveRx.) at various concentrations-0.1×, 0.5×, 1×, 2× and 5× at room temperature on a rocking platform for two hours. Upon completion of this incubation period, 100 µL of a 20 mg/mL stock of X-gal (5-bromo-4-chloro-3-indolyl β-D-galactopyranoside) was added to the plastic dish and the EA/Substrate mixture was incubated at room temperature until bands were detected. When using a luminescent substrate in place of the chromagenic substrate, the incubation period on the blot was 15 minutes at room temperature and the blot was then exposed on a UVP EpiChem II darkroom imager for 5-30 minutes to obtain the results.

To demonstrate a correlation between the amount of EA used in a reaction and the EFC generated signal, a titration of EA amounts was performed. Total cell lysate from either HeLa or HeLa cells transfected with STAT-PL or CyclinD1-PL were run on a 4-12% Bis-Tris gel. The samples were transferred to nitrocellulose and then separately incubated with different concentrations of EA (5×, 2×, 1×, 0.5× and 0.1×) for two hours. The blots were then incubated with X-gal substrate overnight to produce a chromagenic signal. An EFC signal was detected using EA at a concentration as low as 0.5×. There is very low background signal as only ProLabel tagged products produce a signal on the membrane. Two different ProLabel tagged genes (STAT1 and CyclinD1) were used to transfect into HeLa cells. The control lanes used in each condition were HeLa cells transfected with the pCMV-PL plasmid alone. ProLabel expressed in mammalian cells by itself is degraded, while ProLabel tagging a protein results in a stable product that can be detected by EFC.

Equivalent amounts of total protein were run in triplicate on a 4-12% Bis-Tris gel. A Western transfer was performed as described above. The nitrocellulose membranes were incubated with different concentrations of EA solution for 2 hours at room temperature and then X-gal substrate was added and the blots were incubated overnight.

RNA interference (RNAi) technology has become a commonly used method to examine the specific gene silencing in different cell types. The process involves either small hairpin RNAs (shRNAs) generated by plasmid expression vectors or chemically synthesized antisense oligos to targeted genes being introduced into cells via transfection. The interfering RNA binds to the complementary sequence of the expressed gene of interest which causes a cascade of events leading to the eventual degradation of the target mRNA and silencing of gene expression. To analyze the effects of RNAi introduced into a cell, two methods are commonly used: PCR to monitor mRNA levels or standard Western analysis and antibody detection. Both are well established procedures, but they have their drawbacks. PCR is only a monitor of mRNA levels and cannot account for translational modifications that can affect the expression and function of the gene of interest. Western analysis is limited to the specificity of the antibody to detect the protein of interest. The following sets of experiments demonstrate the application of EAstern analysis to measure the expression of different ProLabel tagged genes subjected to RNAi technology. A comparison of the results obtained by EAstern and Western analysis is shown.

Figure 5:
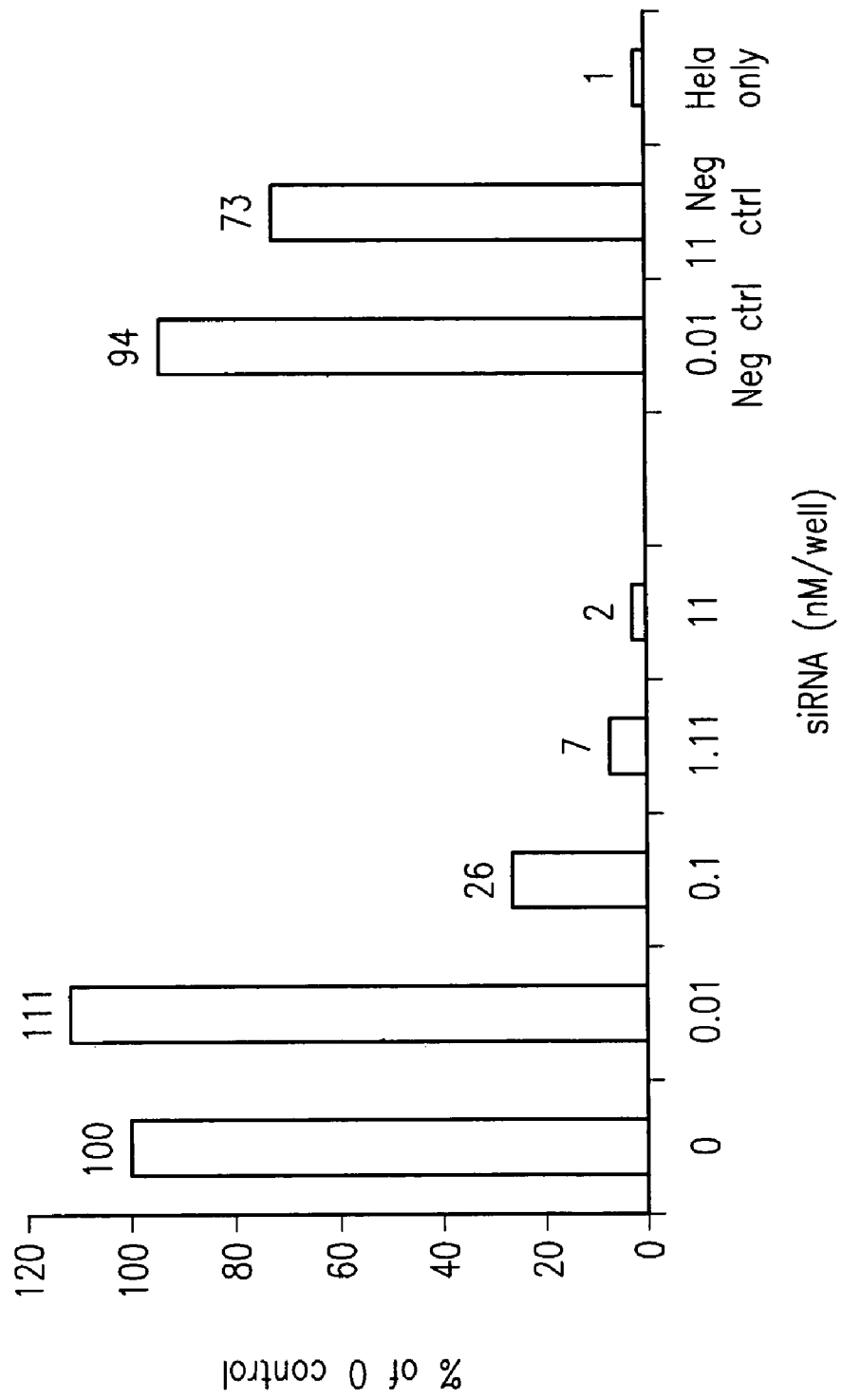
FIG. 5 shows a bar graph of expression of p53-PL in the presence of varying amounts of siRNA (in specification)

In this first experiment, a pool of siRNAs specific for p53 and p53-PL plasmid DNA (DiscoveRx) was used to co-transfect HeLa cells. The p53 siRNA pool contained an equivalent mixture of four oligos that were specific and complementary to p53 RNA sequences (Dharmacon, cat # Q-003946-00-09). The negative control siRNA is a nonsense scrambled oligo sequence (Dharmacon, cat # D-001206-13-05) which was also tested at similar concentrations (11 and 0.11 nM). The cells were collected 16 hours post transfection, resuspended in 500 µL of cell lysis buffer (DiscoveRx) and incubated at 37° C. for 30 minutes. To test for EFC activity of the different conditions, 30 µL of a 1:10 dilution of the cell lysate from each test condition was incubated with 20 µL of 2× EA for 15 minutes at room temperature in a 384 well plate. To this reaction, 30 µL of chemiluminescent substrate (DiscoveRx/ABI, Galacton star and Emerald II enhancer mixed together according to supplier's protocol) was added and the plate was read after 30 minutes incubation at room temperature. The results as shown in FIG. 5 show that EFC activity of p53-PL is reduced (as much as 98% at the highest concentration) when increasing concentrations of p53 siRNA is introduced into the cell. The negative control siRNA had minimal effect on p53-PL expression as measured by EFC activity.

As shown in FIG. 5, Hela Cells were co-transfected with p53-PL (0.5 µg/well) and increasing amounts of the siRNA pool to p53 (0.01-11 nM/well) described above. The procedure was performed as described above. (A) EFC activity demonstrated the effect of the siRNA reducing the expression of the ProLabel tagged p53 gene. (B) Western and EAstern analysis was performed to monitor the levels of p53-PL protein expressed after titrating the amount of the p53 siRNA pool. The results of the EAstern and Western were in agreement with the EFC data. The EAstern results had a very specific band that was detected by the EA/X-gal substrate, while the Western had higher levels of non-specific binding/background on the blot.

TABLE 1 summarizes data from FIG. 5:

| SiRNA (nM/well) | P53 siRNA Pool | | | |
|---|---|---|---|---|
| | R1 | R2 | R3 | Avg |
| 0 | 12810 | 15197 | 17114 | 15040 |
| 0.01 | 17836 | 18116 | 14348 | 16767 |
| 0.1 | 5082 | 3757 | 3002 | 3947 |
| 1.11 | 1341 | 1029 | 796 | 1055 |
| 11 | 314 | 321 | 294 | 310 |
| 0.01 Neg Ctrl | 19600 | 13252 | 9701 | 14184 |
| 11 Neg Ctrl | 10600 | 11987 | 10241 | 10943 |
| Hela only | 190 | 219 | 214 | 208 |

Figure 6:
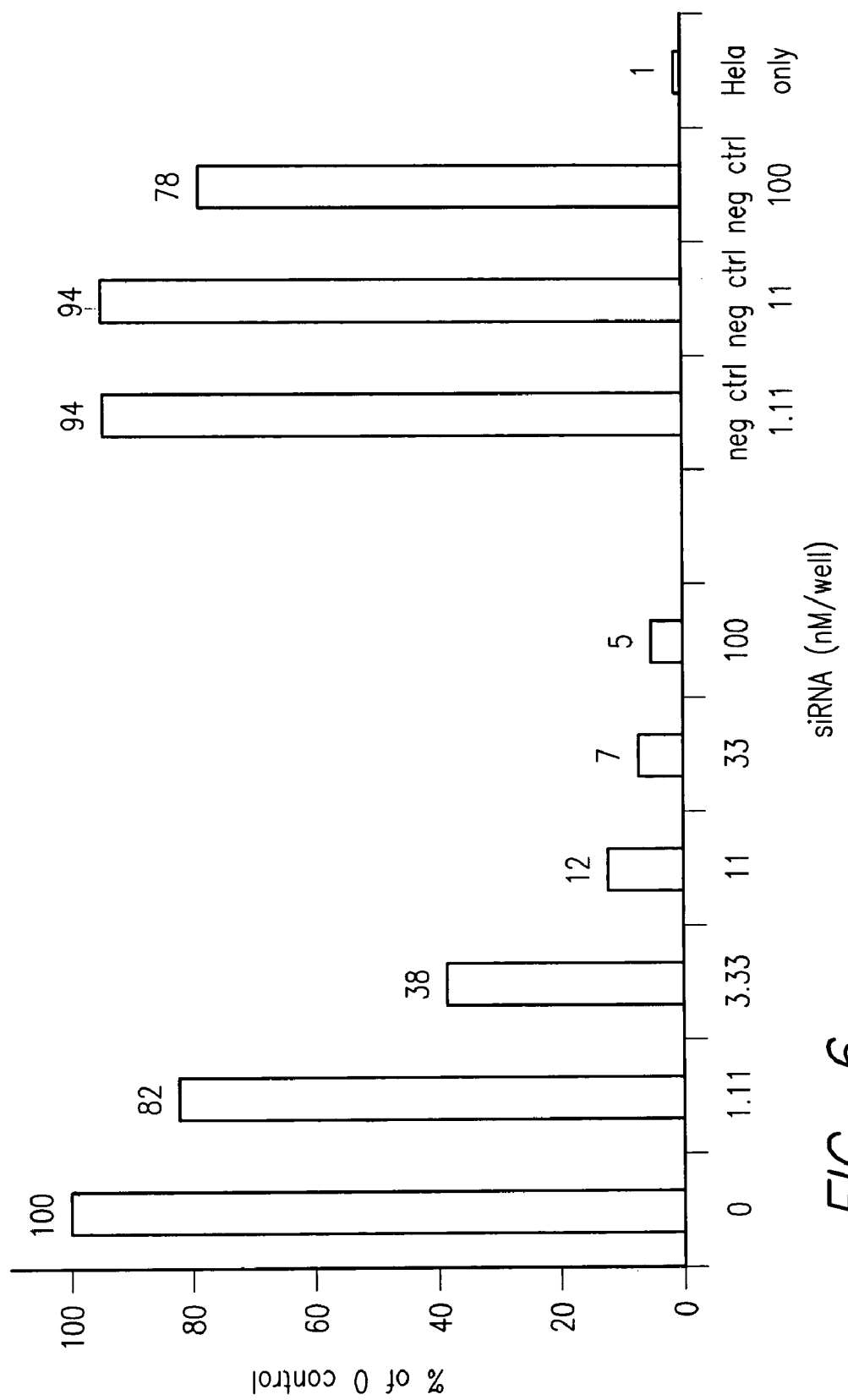
FIG. 6 shows a bar graph of the effect of siRNA on cyclin-D1-PL expression (in specification)

The next experiment was testing an siRNA pool to Cyclin D1 (Genbank accession # NM_053056). HeLa cells were co-transfected with Cyclin D1-PL plasmid DNA (0.5 µg/well) and increasing amounts (1.11-100 nM/well) of siRNA to Cyclin D1 (Dharmacon, cat. # M-003210). The procedure for transfecting, collecting and assaying the cells was carried out as described above. As seen in FIG. 6, introduction of the siRNA pool to Cyclin D1 at 1.11 nM generated almost a 90% decrease in the EFC signal. The negative control siRNA (same as used in previous experiment) did not dramatically reduce the EFC activity of Cyclin D1-PL. A Western was performed on the lysate material probing the blot with α-Cyclin D1 (Upstate, cat # 60-068) and β-Actin antibodies (AbCam cat # AB6276-100) as a control for protein loading. The Western analysis showed a loss of the detected Cyclin D1-PL band (~41 kDa). The detected signal titration with the Cyclin D1 siRNA was not as evident in the Western. However, with the EAstern analysis, a distinct Cyclin D1-PL band was observed and a titration of this signal down to 11 nM/well was observed.

As shown in FIG. 6, SHeLa Cells were co-transfected with CyclinD1 carboxyl-terminally tagged with ProLabel and increasing amounts of an siRNA pool to Cyclin D1 (Dharmacon, cat. # M-003210) using Lipofectamine 2000 reagent (Invitrogen). EFC activity was measured by testing a 1:10 dilution of the lysate. Western and EAstern analysis were performed to monitor the levels of Cyclin D1-PL protein expressed after titrating the amount of the Cyclin D1 siRNA pool. The EAstern and Western data support the EFC results. The EAstern results had a very specific band of expected size for Cyclin D1-PL that was detected by the EA/X-gal substrate that titrated with the concentration of the siRNA tested. The Western blot produced a band of interest, but the intensity and titration of the detected band did not follow the titration of the siRNA treatment as well as the EAstern.

TABLE 2 summarizes data from FIG. 6:

| | Cyclin 01 siRNA pool | | | | | |
|---|---|---|---|---|---|---|
| | R1 | R2 | R3 | R4 | Avg | Normalize to 0 cond. |
| 0 | 548368 | 538663 | 520175 | 528248 | 533864 | 100 |
| 1.11 | 408751 | 451472 | 440143 | 451496 | 437966 | 82 |
| 3.33 | 196283 | 217857 | 211138 | 193343 | 204655 | 38 |
| 11 | 61112 | 65452 | 67054 | 63796 | 64354 | 12 |
| 33 | 36013 | 40026 | 40047 | 38053 | 38535 | 7 |

TABLE 2-continued summarizes data from FIG. 6:

Cyclin 01 siRNA pool

|  | R1 | R2 | R3 | R4 | Avg | Normalize to 0 cond. |
|---|---|---|---|---|---|---|
| 100 | 27205 | 30272 | 28687 | 27471 | 28409 | 5 |
| neg ctrl 1.11 | 466152 | 508028 | 512106 | 520090 | 501594 | 94 |
| neg ctrl 11 | 478612 | 517786 | 539885 | 478485 | 503692 | 94 |
| neg ctrl 100 | 394605 | 429002 | 441383 | 406290 | 417820 | 78 |
| Hela only | 2764 | 2925 | 2903 | 2790 | 2846 | 1 |

Figure 7:
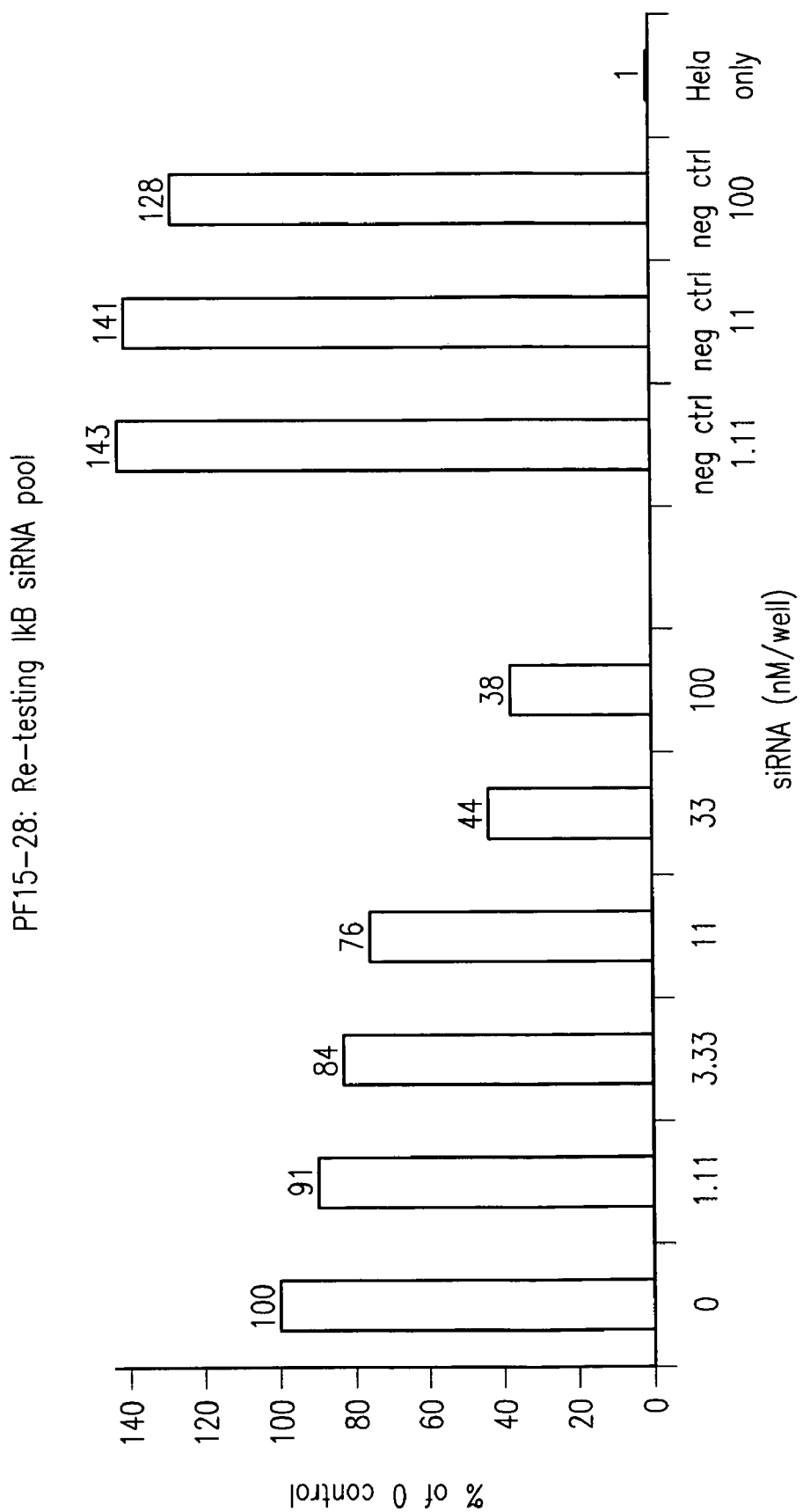
FIG. 7 shows a bar graph of the effect of siRNA on Iκβ-PL expression (in specification)

The next experiment performed was testing a siRNA pool specific to Iκβ (GenBank accession # NM_010546). As done in the previous experiments, Iκβ-PL plasmid (0.5 μg/well) was co-transfected with increasing concentrations of a siRNA pool specific to Iκβ (Dharmacon, cat # M-004765) as well as non-specific negative control pool siRNA (Dharmacon, cat # D-001206-13-01). A portion of the transfected cell lysate was tested for EFC activity. A dose dependent response to the Iκβ specific siRNA pool was observed. The data suggests that the even at the highest concentrations of the siRNA pool, there is only ~62% reduction in EFC activity (FIG. 7). This may be due to the 16 hour post transfection incubation period with the siRNA and that a longer incubation would result in a larger silencing of the Iκβ mRNA. The Western and Eastern blots both show a decrease in detected signal for Iκβ-PL that is similar to the results seen with the EFC data. The EAstern detected two bands for Iκβ-PL, which could represent constitutively expressed and phosphorylated forms of the protein. With the Western analysis, both the endogenous as well as the ProLabel tagged forms of IκB were detected. The background signal on the Western blot was higher than that observed for the EAstern analysis.

Results from FIG. 7 are summarized in Table 3 below.

IkB siRNA pool

|  | R1 | R2 | R3 | R4 | Avg | Normalize to 0 cond. |
|---|---|---|---|---|---|---|
| 0 | 529001 | 518077 | 497526 | 475631 | 505059 | 100 |
| 1.11 | 433412 | 464057 | 451296 | 483546 | 458078 | 91 |
| 3.33 | 442236 | 430682 | 415736 | 407296 | 423988 | 84 |
| 11 | 402944 | 380830 | 370409 | 380952 | 383784 | 76 |
| 33 | 220686 | 220305 | 222427 | 232435 | 223963 | 44 |
| 100 | 195320 | 196964 | 185139 | 185962 | 190846 | 38 |
| neg ctrl 1.11 | 681262 | 726399 | 745012 | 735201 | 721969 | 143 |
| neg ctrl 11 | 689056 | 721891 | 705684 | 727024 | 710914 | 141 |
| neg ctrl 100 | 614517 | 682034 | 613481 | 669991 | 645006 | 128 |
| Hela only | 2920 | 3180 | 3068 | 2886 | 3014 | 1 |

Hela Cells were co-transfected with Iκβ-PL(0.5 μg/well) and increasing amounts of an siRNA pool to Iκβ (0.01-100 nM/well). The procedure was performed as described above. EFC activity demonstrated the effect of the siRNA reducing the expression of the ProLabel tagged Iκβ gene (A). Western and EAstern analysis was performed to monitor the levels of Iκβ-PL protein expressed after titrating the amount of the IκB siRNA pool (B). The EAstern and Western data support the EFC results showing a reduction in the detected levels of Iκβ-PL.

Figure 8:
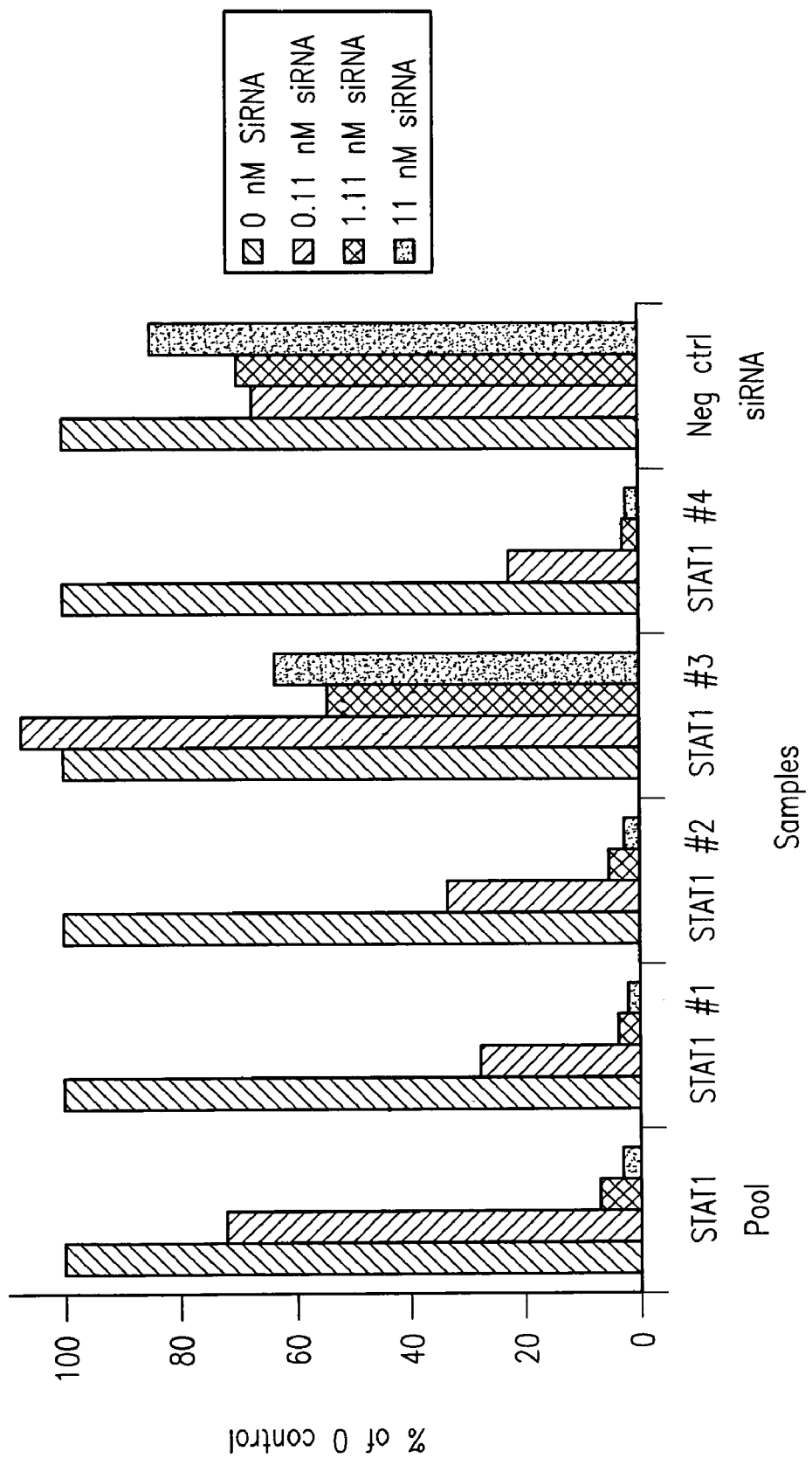
FIG. 8 shows a bar graph of the effect of siRNA on STAT-1-PL expression (in specification).

In this example, the STAT1 gene (GenBank accession # NM_032612) was tagged with ProLabel. This plasmid construct (0.5 μg/well) was co-transfected into HeLa cells titrating the amount of either a pool of 4 different specific individual siRNAs to STAT 1 (Dharmacon cat. #M-004718-00-50) at equilivalent concentration or each individual siRNA to STAT1 at that same concentration. The negative control siRNA is a nonsense scrambled oligo sequence (Dharmacon, cat # D-001206-13-05) which was also tested at similar concentrations (11, 1.11, 0.11 nM). The cells were collected 16 hours post transfection, resuspended in 500 μL of cell lysis buffer (DiscoveRx) and incubated at 37° C. for 30 minutes. As shown in FIG. 8, co-transfection of STAT1-PL plasmid DNA along with increasing concentrations of the pool and individual STAT1 siRNAs (except for individual siRNA #3) resulted in a reduction of greater than 90% EFC activity as measured by monitoring STAT1-PL activity. The negative control scrambled siRNA never had greater than 25% reduction in EFC of the STAT1-PL. These results were also confirmed by Western analysis using an α-STAT1 antibody (Cell Signaling Technologies, Cat # 9176) and EAstern analysis. The endogenous STAT1 as well as the ProLabeled tagged STAT1 were detected by the Western analysis. The EAstern detected a single distinct band for STAT1-PL. The trend of seeing a reduction or loss of STAT1-PL detection based on the individual siRNA treatments was displayed. The individual STAT1 siRNA #3 did not affect expression compared to the other individual siRNAs that had over 70% reduction in EFC activity at 0.11 nM/well. This was also shown by the Western and EAstern analysis.

Lysates from HeLa cells co-transfected with STAT1-PL and three different concentrations of the pool and individual STAT1 siRNAs as well as negative control siRNAs were assayed for EFC activity in a 384 well plate format following the protocol described above. A portion of the lysates was also run on 4-12% Bis-Tris gels, and subjected to Western and EAstern analysis, again following the procedure listed above.

The results from FIG. 8 are summarized in Table 4 below:

|  | 0 | 0.11 | 1.11 | 11 |
|---|---|---|---|---|
| STAT1 Pool | 100.0 | 72.2 | 6.7 | 2.8 |
| STAT1 #1 | 100.0 | 27.6 | 3.8 | 2.2 |
| STAT1 #2 | 100.0 | 33.9 | 5.7 | 3.1 |
| STAT1 #3 | 100.0 | 108.6 | 55.0 | 64.3 |
| STAT1 #4 | 100.0 | 23.4 | 3.4 | 2.8 |
| Neg Ctrl siRNA | 100.0 | 68.2 | 71.0 | 86.0 |

The following experiments were performed using a bacterially expressed and column purified form of glutathione-S-transferase tagged with ProLabel (GST-PL). GST-PL was purified to >80% homogeneity as determined by Commassie brilliant blue staining and the concentration of the material was determined by spectrophotometric $A_{280}$ absorbance reading. For all experiments, the GST-PL and the GST alone (control) were diluted in a total cell lysate isolated from $5 \times 10^6$ cells/mL of CHO-K1 mammalian cells.

In the first example, the bacterial GST fusion expression constructs: pGEX-6P1 (Amersham) and pGEX-6P-1+ Pro-Label were grown to log phase (as determined by $OD_{600}$ reading) at 37° C. and then induced with 0.5 mM IPTG (final concentration) overnight at 37° C. The cells were collected and lysed by sonication, clarified by centrifugation and the supernatant was retained. This material was incubated with 200 μL of α-GST-sepharose resin rocking for 1 hour at 4° C. The resin was pelleted, washed 3× with PBS+1× protease inhibitor cocktail. The GST fusion protein was eluted from the resin with 10 mM reduced glutathione (made up in 50 mM Tris-pH8.0). Approximately 5 ng of GST or GST-PL fusion protein was run on three 4-12% Bis-Tris acrylamide gels. One gel was stained with Coomassie brilliant blue stain. The other two gels were subjected to electrotransfer to nitrocellose membrane. One gel was probed with an anti-GST polyclonal antibody—Western analysis. The Western analysis was done using a 1:7500 dilution of the anti-GST polyclonal antibody (Amersham, cat.# 27-4577-01), incubated overnight at 4° C. The next day, the blot was washed 3× in PBS+0.01% Tween 20 and probed with a secondary antibody (Donkey anti-Goat IgG-HRP, 1:10000 dilution, Promega cat. # V805A), washed 3× with PBS+0.01% Tween 20 and developed following the protocol of the Pierce Supersignal West dura extended duration substrate (Pierce, cat # 34075). The other blot was used for an EAstern analysis. The EAstern was incubated with 5× EA for 1 hour and then 100 μL of a 20 mg/mL stock of X-gal was added to the blot and incubated on a rocker at room temperature. The GST-PL band was detected ~3 hours after the addition of the X-gal substrate.

Full-length GST-PL product as well as GST alone and the degradation products were detected by α-GST Western analysis. The EAstern analysis detected a single band of the correct size for GST-PL (~33 kDa).

Purified GST and GST-PL (5 ng) were diluted in CHO-K1 cell lysate and run on SDS-PAGE. The gel was either Coomassie brilliant blue stained (A) or transferred to nitrocellulose membrane for Western (B) or EAstern (C) analysis. The EAstern had a clear single band at 38 kD with GST-PL and no band with GST, the Western had a number of diffuse bands with GST-PL and the Coomassie brilliant blue showed a band at 38 kD with GST-PL and 28 kD with GST. Blots are shown in the indicated panels in the priority provisional patent application.

To increase the sensitivity of EAstern detection, a chemiluminescent substrate, Promega Beta-Glo (catalog # E4740), was tested. The luminescent substrate was substituted for X-gal in the assay protocol to take advantage of the amplifiable enzymatic reaction of EFC activity to increase the detection sensitivity and possibly reduce the time needed to detect a signal (4-24 hour exposure time). The Promega substrate utilizes a luciferin-galactoside substrate (6-O-β-galactopyranosyl-luciferin). Upon ProLabel and EA forming an active β-galactosidase complex it will cleave the substrate to form luciferin and galactose. The luciferin is then utilized in a firefly luciferase reaction to generate light. With GST or GST-PL run on SDS-PAGE, the Promega substrate works well with the EAstern protocol in being able to detect the PL tagged gene of interest as a distinct band. The amount of GST and GST-PL was titrated from 2.5 to 0.09 ng/lane. The proteins transferred to nitrocellulose membrane were incubated with ~5 mL of 5× EA solution (DiscoveRx) for either 2 or 4 hours and then with 3 mL of the Promega substrate for 15 minutes. Bands were clearly detected in the GST-PL sample lanes by 30 minutes of exposure time on the UVP imager. The level of detection was 0.09 ng of GST-PL protein with a 2 or 4 hour preincubation with 5× EA and a 60 minute exposure when using the luminescent substrate.

Various concentrations of either GST or GST-PL (0.09 ng to 2.5 ng/lane) were loaded onto a 4-12% Bis-Tris gel. A standard Western transfer was performed and the samples were then incubated with 5× EA for 2 or 4 hours followed by 15 minute incubation with the Promega prototype Beta-Glo substrate. 30 and 60 minute exposures on the gel imager were made. A 4 hour incubation with EA and then the Beta-Glo substrate with a 60 minute exposure was able to clearly detect 0.28 ng lane of the GST-PL protein and faintly could detect 0.09 ng.

The next experiment addresses the question if mixing EA and luminescent substrate together would provide a similar detected signal to that seen by adding each component separately. This would reduce one incubation period and shorten the protocol by 1-2 hours. GST and GST-PL were run on SDS-PAGE and probed with a 4:1 mixture of 5× EA: Promega luminescent substrate, for one or two hours before being exposed on the imager for 30 or 60 minutes. With a 60 minute exposure, a titration of the GST-PL from 2.5 to 0.09 ng can be detected.

GST or GST-PL (0.09 ng to 2.5 ng/lane) samples were loaded onto a 4-12% Bis-Tris gel. A standard Western transfer was performed and the samples were than incubated with a 4:1 mixture of 5× EA: Promega prototype Beta-Glo substrate for 1 or 2 hours. 30 and 60 minute exposures on the gel imager were made. Both the 1 and 2 hour incubation of EA/Substrate with a 60 minute exposure showed detection of GST-PL at 0.09 ng per lane. There were very few non-specific bands that appeared. No non-specific background bands were seen in the GST alone or the CHO-K1 only (CHO) lysate.

To address if detection of an EAstern signal is dependent upon the type of membrane used, a comparison of nitrocellulose versus polyvinylidene fluoride (PVDF) membrane was made. Increasing concentrations of GST and GST-PL were run on SDS-PAGE, and a Western transfer was performed to each membrane type. The four separate blots were pre-incubated with 5× EA for 1 hour and then incubated with the Promega substrate for 15 minutes. Or, a 4:1 mix of EA and substrate was made and incubated on the blots for 1 hour. With a 10 minute exposure, both membranes showed strong bands in which the detected signal was titrating with the concentration of protein run. There appears to be a more distinct signal with less background on the PVDF membrane versus the nitrocellulose.

Two different incubation periods with EA and substrate were tested. Also, two different types of membranes were compared, nitrocellulose and PVDF. First 5× EA was mixed (4:1) with the luminescent substrate and added to the two different types of membranes for 1 hour and the results were measured over time. The CHO-K1 lysate used to dilute the GST and GST-PL protein was also run on the gel to demonstrate there was no non-specific products generated from the lysate. A 10 minute exposure on the imager was used. Second a duplicate set of membranes were pre-incubated with 5× EA for 1 hour and then incubated with the luminescent substrate for 10 minutes and then a 10 minute exposure was taken on the imager. The data suggest that similar results were observed with either mixing EA and substrate or performing a pre-incubation with EA and then adding the substrate for a short period. However, there appeared to be a more distinct signal with less background on the PVDF membrane versus the nitrocellulose.

To demonstrate the lowest level of detectable protein by EAstern analysis, another titration (0.28-0.01 ng) of GST and GST-PL protein was run on SDS-PAGE. Western transfer of the gels was carried out onto nitrocellulose membrane. The blots were incubated with 3 mL of either 2× or 5× EA for 1 hour followed for 15 minutes with 2 mL of Promega Beta-Glo substrate. The blots were exposed for either 5 or 10 minutes. The data shows that with either 2× or 5× EA that a distinct GST-PL band is detected at a concentration as low as 0.03 ng.

GST and GST-PL were run on 4-12% Bis-Tris gels, Western transfer was done and EAstern analysis performed. The membranes were incubated with 3 mL of 2× or 5× EA reagent for 1 hour and then 2 mL of Promega Beta glo substrate. The blots were then exposed for either 5 or 10 minutes. There is a distinct band for GST-PL that is seen with the 2× EA as low as 0.03 ng. There is more smearing of the sample when 5× EA is used.

A head to head comparison of EAstern and Western analysis was performed. Duplicate gels were run with different amounts (0.03-0.71 ng) of GST and GST-PL. EAstern analysis was performed using 5× EA incubated for 1 hour and then 15 minutes with the luminescent substrate and 10 minute exposure. A distinct GST-PL band of the correct size was detected by EAstern at each of the different concentrations. The Western was able to detect GST and GST-PL at each of the concentrations. However there was a higher level of non-specific background on the blot. This could be due to the primary and secondary antibody concentrations used and further analysis would need to be done.

GST and GST-PL were run on SDS-PAGE and Western transferred to nitrocellulose. EAstern and Western analysis were performed as described above. In the case of the EAstern, the membrane was exposed for 3 minutes under the UVP imager. The Western transfer was exposed for 1 minute under the UVP imager. The EAstern showed only a single band, while numerous bands were observed with the Western, including both the 28 kD and the 38 kD bands.

It is evident from the above results that the subject system allows for following the fate of a protein as part of the natural metabolism, as affected by a change in the expression of another protein or as affected by a change in the external or internal environment. The system is particularly powerful when used in conjunction with the Eastern method, as allowing for a simple protocol and ready comparison of a number of different results evaluated under the same conditions. The subject system provides for an analysis of the various ways that a protein may be modified intracellularly during its lifetime, providing a snapshot of the state of the protein during the cellular evolution. Where all of the cells are in the same state, then one obtains the protein profile at the time of the analysis. Where the cells are in different states, then one obtains a picture of the history of the protein during the life of the cell.

The EAstern method for detecting the effect of changes in environment on the state of an intracellular protein is highly sensitive and offers many advantages over conventional Western analysis. The methodology allows for detection of extremely small amounts of intracellular proteins carrying the ED label, so that the various forms of the modified target protein can be observed, such as ubiquitination and polyubiquitination, partial degradation products, addition or removal of small functional groups, such as phosphate, acetyl, etc. The method is readily applicable to high throughput screening, providing substantially analogous steps to the Western. The additional step of transforming a cell with the fusion protein construct can be performed commercially and such cells made available for individual proteins or can be readily performed by those of ordinary skill in the art. The subject method provides an important advance and advantage to the efforts to understand cellular processes, their response to changes in the environment and the ability to rapidly screen compounds for physiological effect, providing the opportunity for monitoring changes over time.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for performing a Western blot for determining modification of an intracellular target protein in a transfected cell using a fusion protein serving as a surrogate protein for said-target protein, said surrogate protein comprising an enzyme donor (ED), wherein said ED is a member of an enzyme fragment complementation pair of β-galactosidase that forms an active enzyme with the complementary enzyme acceptor fragment (EA) and said surrogate protein is modified in said cell in the same manner as said target protein, said modification occurring as a result of changes in the environment of said cell where said modifications result in a change in the migration rate of said surrogate protein in gel electrophoresis, wherein said method comprises:

lysing said transfected cell, transformed with an expression construct of said fusion protein resulting in intracellular expression of said fusion protein, to form a lysate;

separating said lysate by gel electrophoresis into bands where said fusion protein and intracellular modifications thereof comprising said ED are separated by at least one of size and mass-to-charge ratio;

transferring said bands to a membrane;

adding EA and substrate to said membrane to visualize modified and unmodified fusion protein bands free of other bands; and determining from said bands whether said target protein is modified as a result of said changes in the environment of said cell.

2. A method according to claim 1, wherein said ED is less than about 100 amino acids.

3. A method according to claim 1, wherein said ED is at the C-terminus of said target protein.

4. A method according to claim 1, further comprising, prior to lysing said cell, further comprising the step of contacting said cell with an agent to determine the effect of said agent on the state of said target protein in said cell.

5. A method according to claim 4, wherein said agent-acts to provide RNA interference (RNAi) for a protein other than said target protein.

6. A method according to claim 1, including the additional step of determining a natural target protein on said membrane.

7. A method according to claim 1, wherein said Western blot employs a polyvinyldifluoride (PVDF) membrane.

8. A method according to claim 1, wherein said Western blot employs a nitrocellulose membrane.

9. A method according to claim 4, wherein said agent is a candidate drug.

10. A method according to claim 1, wherein said changes are selected from the group consisting of degradation, phosphorylation, glycosylation or acylation.

* * * * *